(12) United States Patent
Selby et al.

(10) Patent No.: US 10,448,623 B1
(45) Date of Patent: Oct. 22, 2019

(54) HABITAT AND SYSTEM FOR CULTIVATION OF INSECTS

(71) Applicant: Aspire Food Group USA Inc., Austin, TX (US)

(72) Inventors: Roger Duncan Selby, Austin, TX (US); Michael Todd Hall, Corpus Christi, TX (US); Gabriel Mott, Austin, TX (US); Paul T. Williams, Austin, TX (US); Redza Shah, Austin, TX (US); Anna D. Cardinal, Austin, TX (US)

(73) Assignee: Aspire Food Group USA Inc., Austin, TX (US)

( * ) Notice: Subject to any disclaimer, the term of this patent is extended or adjusted under 35 U.S.C. 154(b) by 365 days.

(21) Appl. No.: 15/486,636

(22) Filed: Apr. 13, 2017

Related U.S. Application Data

(60) Provisional application No. 62/321,912, filed on Apr. 13, 2016.

(51) Int. Cl.
*A01K 67/033* (2006.01)

(52) U.S. Cl.
CPC .................. *A01K 67/033* (2013.01)

(58) Field of Classification Search
CPC .............................. A01K 67/033; A01K 67/00
See application file for complete search history.

(56) References Cited

U.S. PATENT DOCUMENTS

| | | | |
|---|---|---|---|
| 5,351,643 A * | 10/1994 | Hughes | A01K 67/033 119/6.5 |
| 6,568,124 B1 * | 5/2003 | Wilbanks | A01M 1/023 43/112 |
| 8,327,797 B1 * | 12/2012 | Morales-Ramos | A01K 67/033 119/6.5 |
| 2003/0188698 A1 * | 10/2003 | Donaldson | A01K 67/033 119/678 |
| 2015/0027095 A1 * | 1/2015 | Marschall | F02M 35/02458 55/511 |
| 2016/0360741 A1 * | 12/2016 | Gordon | A01M 3/025 |
| 2017/0360014 A1 * | 12/2017 | Hall | A01K 5/02 |
| 2018/0007875 A1 * | 1/2018 | Hall | A01K 67/033 |

\* cited by examiner

*Primary Examiner* — Monica L Williams
(74) *Attorney, Agent, or Firm* — Lee & Hayes, P.C.

(57) ABSTRACT

An insert for use in an insect habitat. The insert usable to increase the overall surface space within a habitat available to cultivate the insects. The insert formed from including a plurality of members formed to mate or otherwise couple together to form a gird.

20 Claims, 29 Drawing Sheets

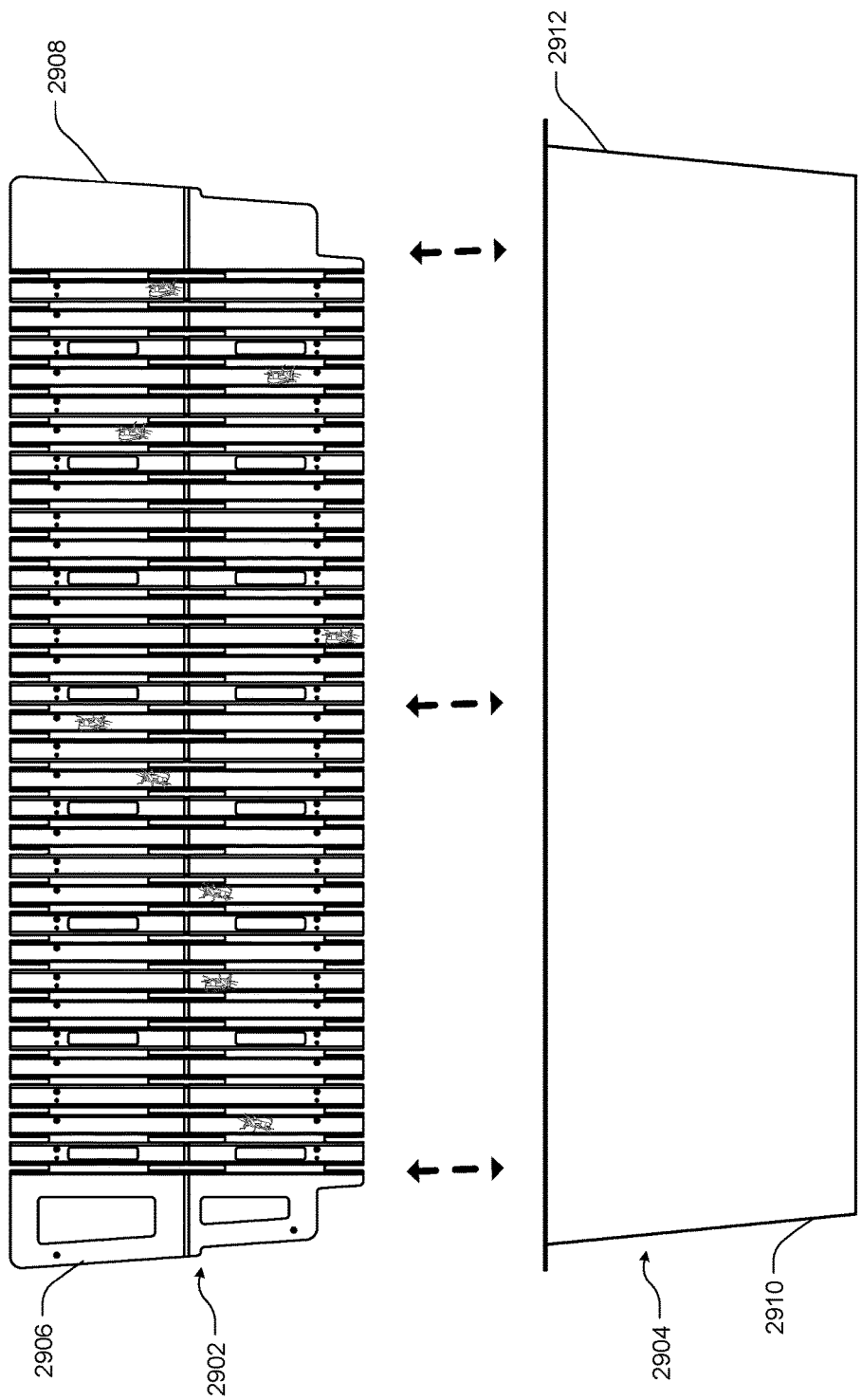

HABITAT AND SYSTEM FOR CULTIVATION OF INSECTS

BACKGROUND

Today most insects that are cultivated for human consumption are housed in single use cardboard boxes or immobile large troughs made of wood or concrete. Cardboard boxes are disposed after each use and add significant expense to the cultivating and harvesting process. Additionally, the cardboard boxes are typically moved around by hand and the insects are watered and fed by hand. This leaves the insects susceptible to damage or loss during the period of time when a human is required to interact with them. For example, the small larva may be removed from the cardboard box with the feeding or watering apparatus during a feeding or watering cycle if the human is not careful. The large troughs made of wood or concrete, are susceptible to pathogenic and fungal activity which may devastate insect populations and materially impede production. This results in substantial economic loss and wastage.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

FIG. 29 illustrates an example of an insert removed from a habitat according to some implementations.

DETAILED DESCRIPTION

Figure 1:
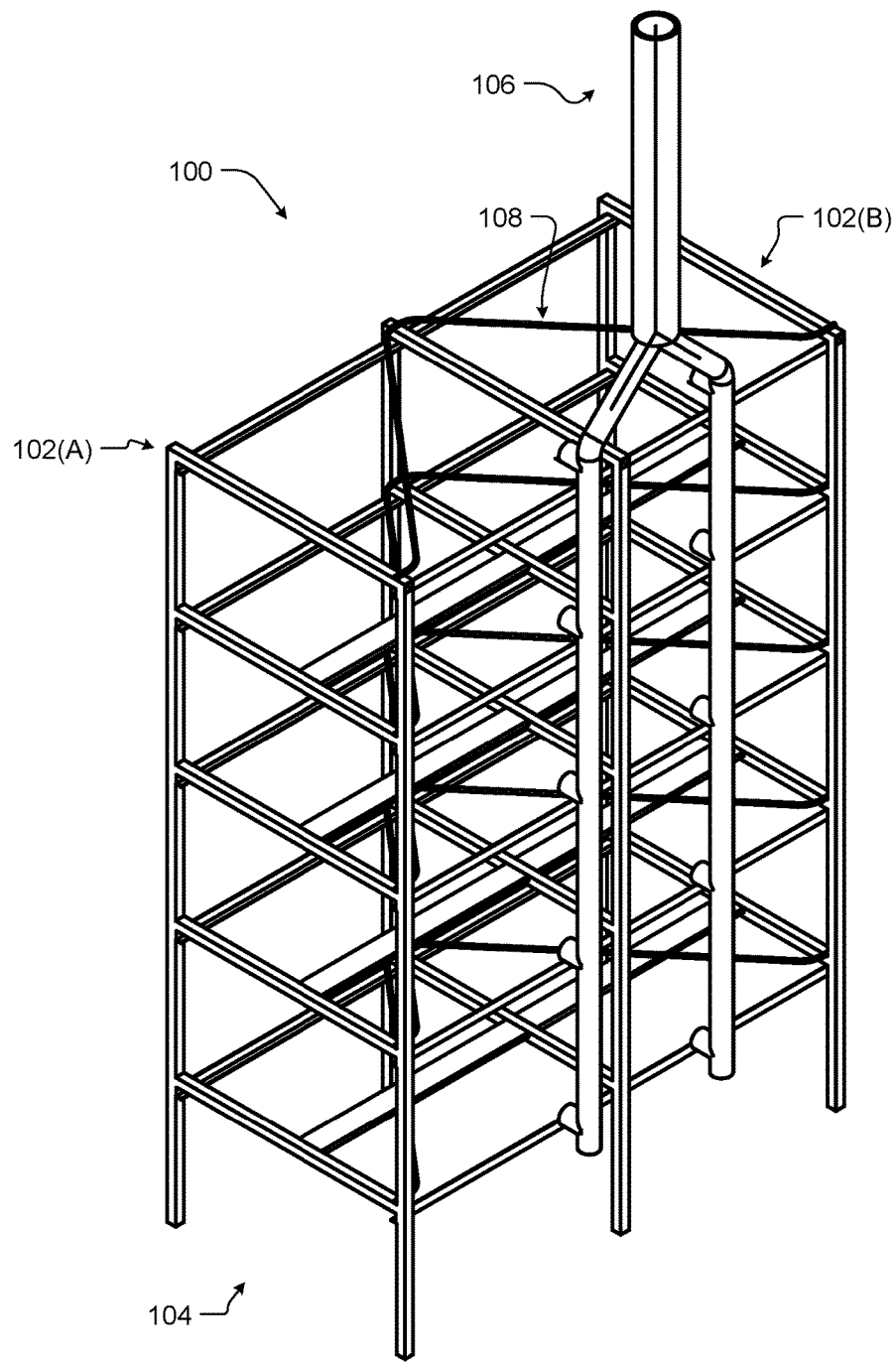
FIG. 1 illustrates an example system for cultivating insects including a rack system and habitat according to some implementations.

Described herein are implementations and techniques for providing an automated habitat and cultivating system for raising insects. For example, the system may include a rack system configured to hold or house multiple insect habitats. In general, the rack system is designed to improve the efficiency of cultivating live insects, such as crickets, grasshoppers, mealworms, and other insects that have a flightless stage, and to minimize the insect's exposure to human interaction or contact in addition to reducing exposure to invasive pathogens. In some examples, the rack system may be include a three-dimensional array of stations for receiving habitats. For example, in some instances, the racks may be configured such that multiple rows of habitats may be arrayed above each other within a rack. Alternately, the rack system may form multiple columns arrayed adjacent to each other. In some cases, each rack of the rack system may be configured to connect or couple to an adjacent rack to form arrays of stations for habits in an X, Y, and Z direction or a cube shaped structure.

In some examples, the habitats are housed along one side or the other of the rack system. The rack system may include multiple levels or tiers formed from a material, such as aluminum, carbon steel, stainless steel, or other material. Each level of the rack system may be configured to hold an habitat such that the habitat may be stacked on top of each other in a manner in which the insects contained in each rack may be isolated from each other. For instance, each level or tier may include insects at different stages of development (e.g., egg, larva, nymph, immature stage, adult, etc.). In some instances, the rack system may include horizontal shelves at each level or tier to support the habitats and allows the habitat to be inserted and removed with little to no human interaction. For example, the shelves may include roller conveyors, skate conveyors, motorized conveyor system or other system for removing and inserting habitats into the shelves.

Additionally, the rack system may be configured to include watering components, feeding components, and lighting components. For example, different insects (such as crickets, grasshoppers, mealworms, and other insects that have a flightless stage) as well as the same insects at different levels of development may require different amounts of water, food, or lighting to achieve improved or substantially optimal growing environments. Thus, in some examples, the rack system may include per level water distribution components or per level food distribution components. For instance, in some cases, the same insects at the same level of development may be stored in habitats within one level or row of the rack system. In this instance, the water distribution components and the food distribution components may provide the same amount of water and/or food to each habitat within the same level of the rack system. Alternatively, the per-rack (or per column) water distribution components or rack (or per-column) food distribution components. For instance, in some cases, water and feed controls may be included in each rack, each row, or each column of the rack system and, thus, provide improved control of food and water distribution per-rack, per-row, or per-column of the system. In this instance, the water distribution components and the food distribution components may provide the same amount of water and/or food to each habitat within the same level of the rack system. Similarly, each rack, row, or column of the rack system may include light mounting components or lighting that may be configured for the particular needs of the insect within the habitat.

The rack system may also include devices, machines, or motors that are configured to move or force the habitats towards the other end of the rack system (e.g., in this manner multiple habitat may be stored along one level of the rack system), thereby, improving the number of habitats per-level and overall efficiency per-space equipment in cultivating the insects. In some cases, a latching mechanism or device may be located at the output of the rack system (e.g., at an end opposite the end at which the habitats are loaded onto the rack) to prevent the habitats from being removed from the rack in an undesired manner.

Thus, in some examples, described herein a rack system that allows for the automation of insect cultivation in a manner that removes human interaction with the insects, which may lead to damage or death of the insects, thereby reducing yields. For example, the rack system described herein allows for the movement of habitats, the lighting of individual habitats, the watering of insects within habitats, and the feeding of the insects within the habitats without direct contact with humans.

It should be understood, that the rack system described herein, is not limited to a single entrance and exit point per-level or tier and that the rack systems may also be constructed with multiple input and output points. In other cases, the rack system may be directed with a unidirectional flow. In these cases, the rack system may be configured to provide isolated clean habitats (or unused) and dirty (or used) containers that reduces the risk of cross-contamination between the habitats. Additionally, the implementations describe herein include no limitation to the number of rows and columns in one rack system.

In the various examples, the rack system is configured to house multiple habitats, either per-row or columns. Each habitat may be designed such that the habitat has a cantilevered lip or bevel to some of, or all, vertical faces. This cantilevered lip allows the insect habitat to be slid onto a storage rack and moved through the rack system. The cantilevered lips are designed such that the lip may withstand gravitational and other physical forces applied to the habitat during use.

In some examples, the habitat is formed from or coated with a material having a low coefficient of friction to mitigate the ability of insects to escape the habitat. For example, the material may have a coefficient of friction less than 0.4, such as Teflon or less than 0.2, such as some polyurethane. In other cases, the material may be or include FDA compliant thermoplastics (such as Radel R, Acrylic, PETG, Polycarbonate, Polysterene, Polysulfone, PVC, Ultem, UHMW-PW, Polpopylene, PTFE, PVDF, PEEK, PBT, Acetal, Nylon, PET, HDPE and LDPE). In some specific examples, the habitat may be formed from a hard plastic material to provide strength and rigidity and the interior surface may be coated, lamented, or otherwise covered by a material having a low coefficient of friction.

The habitat may also be designed with a built in dividing insert or unit. The insert may be included to increase the overall total surface area within the same volume previously contained within the habitat by 25×. The larger the surface area the more insects may be contained or cultivated within a single habitat, thereby improving overall yields per-volume. For example, every two square inches of increased surface area within a habitat has the potential to increase the cricket's population within the habitat by one. In some examples, other designs of inserts may increase the total surface area by other multipliers such as 20×, 30×, or 40×. In one specific example, a habitat may have a total surface area of 1272 inches and the habitat plus the insert may increase the total surface area to 30,998 inches.

The insert or unit contained within the habitat generally form a grid, helix or cross-section within the interior space of the habitat. The insert may be formed from various materials that allow the insects to climb and/or migrate over the vertical walls of the insert. For example, the surface of the insert may be rough or have a high coefficient of friction (e.g., greater than 0.5). Thus, the inserts are able to increase the surface area available to the insects. Additionally, the vertical wall of the insert helps to separate or slow the travel of the insects within the habitat which reduces the risk of pathogenic invasion, spread, and/or exposure to the insects within a single habitat.

In some cases the inserts are designed to be removable from the habitat. Thus the vertical wall design of the inserts may assist with harvesting of the insects when the insert is removed from the habitat. For example, the inserts may be moved over a bin and vibrated to cause the insects to fall off of or detach from the vertical surfaces of the insert.

In some designs, the insert may include notches or depressed regions in the top surface to receive objects at a predetermined location. For example, the notches may be configured to receive feeding or watering apparatuses that are reachable by the insects in a manner that prevents the apparatuses from moving or sliding which may result in damage or death to the insects. The inserts may also include perforations along the interior walls to increase air flow and insect mobility throughout the entire volume and allow the insects to more easily reach the watering and feeding apparatus placed within the habitat. In some cases, the perforations may be at least 0.25 inches by 0.25 inches to allow the insects to pass. In other cases, the perforations may be 0.5 inches by 0.5 inches or 1.0 inch by 1.0 inch.

It should be understood that while the inserts described above include vertical walls, the inserts may be designed to include horizontal walls with or without vertical perforations. In other cases, the insert may include sloping walls or angular walls depending on the type and developmental level of the insects.

FIG. 1 illustrates an example system 100 for cultivating insects including a rack system 102 and habitats, generally indicated by 104, according to some implementations. In this example, two racks 102(A) and 102(B) are positioned adjacent to each other and/or connected to allow the habitats (not shown) to move between the rack 102(A) and the rack 102(B). The system 100 also includes feeding components 106 and watering components 108 for proving an automated environment or habit for the insects within the habitat.

Figure 2:
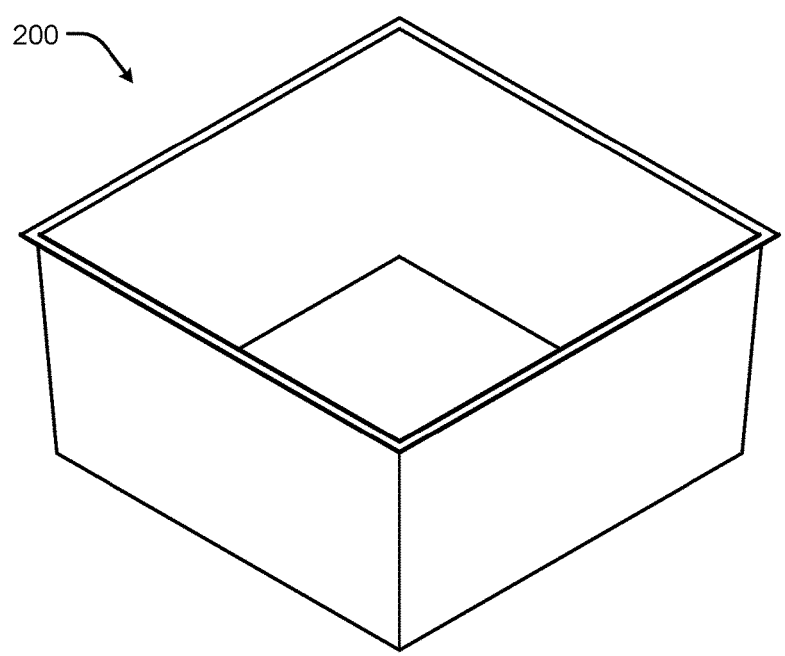
FIG. 2 illustrates an example habitat for use with a rack system for cultivating insects according to some implementations.

FIG. 2 illustrates an example habitat 200 for use with a rack system for cultivating insects according to some implementations. As discussed above, the habitat 200 may be formed from or coated with a material having a low coefficient of friction to mitigate the ability of insects to escape the habitat. For example, the material may have a coefficient of friction less than 0.4, such as Teflon, or less than 0.2, such as some polyurethane. In some specific examples, the habitat may be formed from a hard plastic material to provide strength and rigidity and the interior surface may be coated, lamented, or otherwise covered by a material having a low coefficient of friction.

Figure 3:
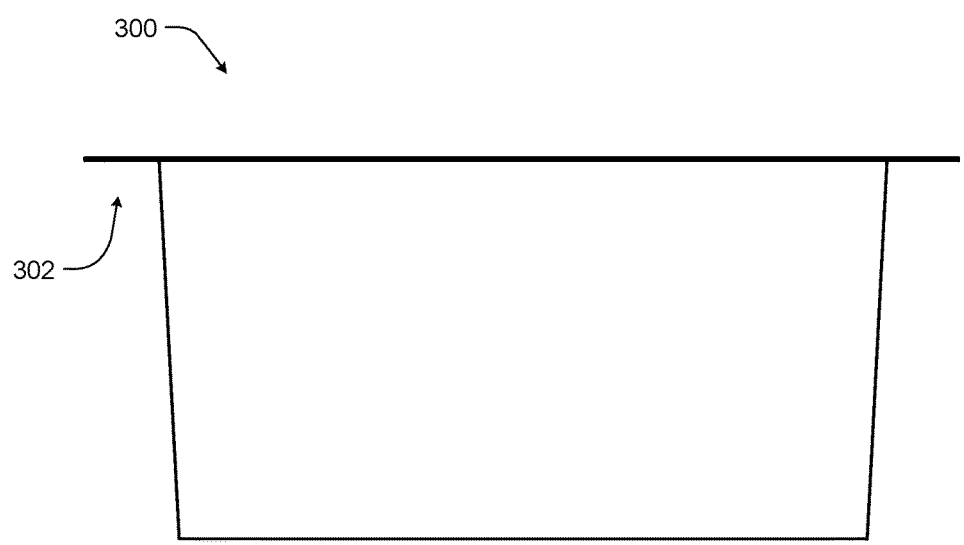
FIG. 3 illustrates another example habitat for use with a rack system for cultivating insects according to some implementations.

FIG. 3 illustrates another example habitat 300 for use with a rack system for cultivating insects according to some implementations. For example, each habitat 300 may be designed such that the habitat 300 has a cantilevered lip or bevel 302 to some of, or all, vertical faces. This cantilevered lip 302 allows the insect habitat 300 to be slid onto a storage rack and moved through the rack system. The cantilevered lip 302 may be designed such that the lip 302 may withstand gravitational and other physical forces applied to the habitat during uses.

Figure 4:
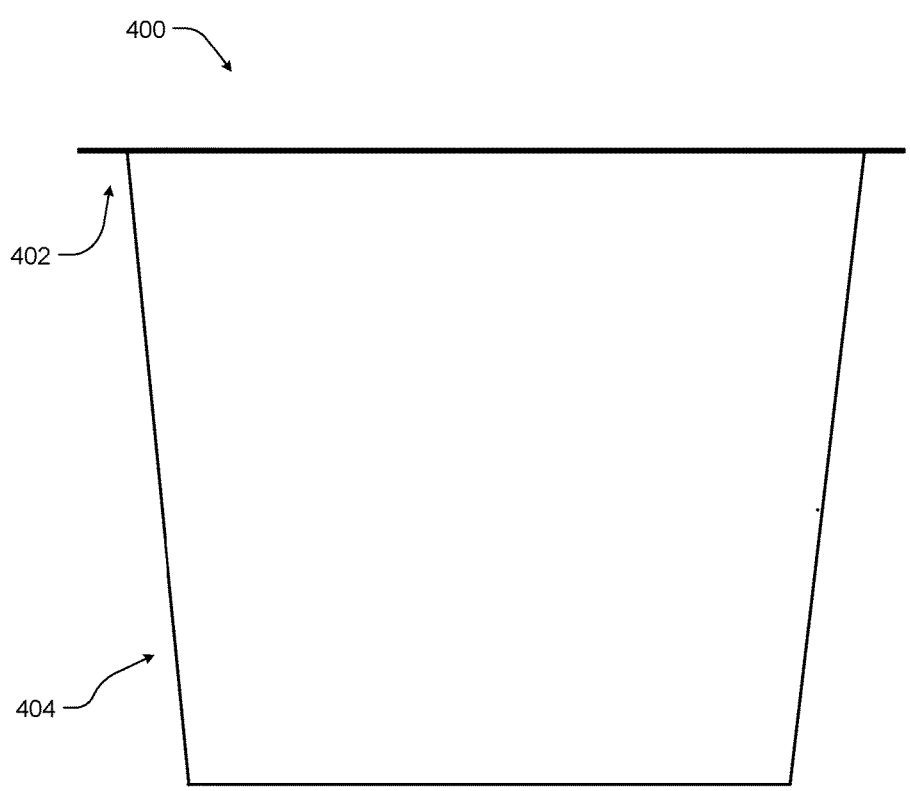
FIG. 4 illustrates yet another example habitat for use with a rack system for cultivating insects according to some implementations.

FIG. 4 illustrates yet another example habitat 400 for use with a rack system for cultivating insects according to some implementations. In the illustrated example, the habitat 400 includes angled side walls 404 in addition to the cantilevered lip 402. The angled side walls 404 may assist in preventing the insects from escaping the habitat 404, particularly when the interior surface of the side wall 404 is coated or formed from a material having a low coefficient of friction.

Figure 5:
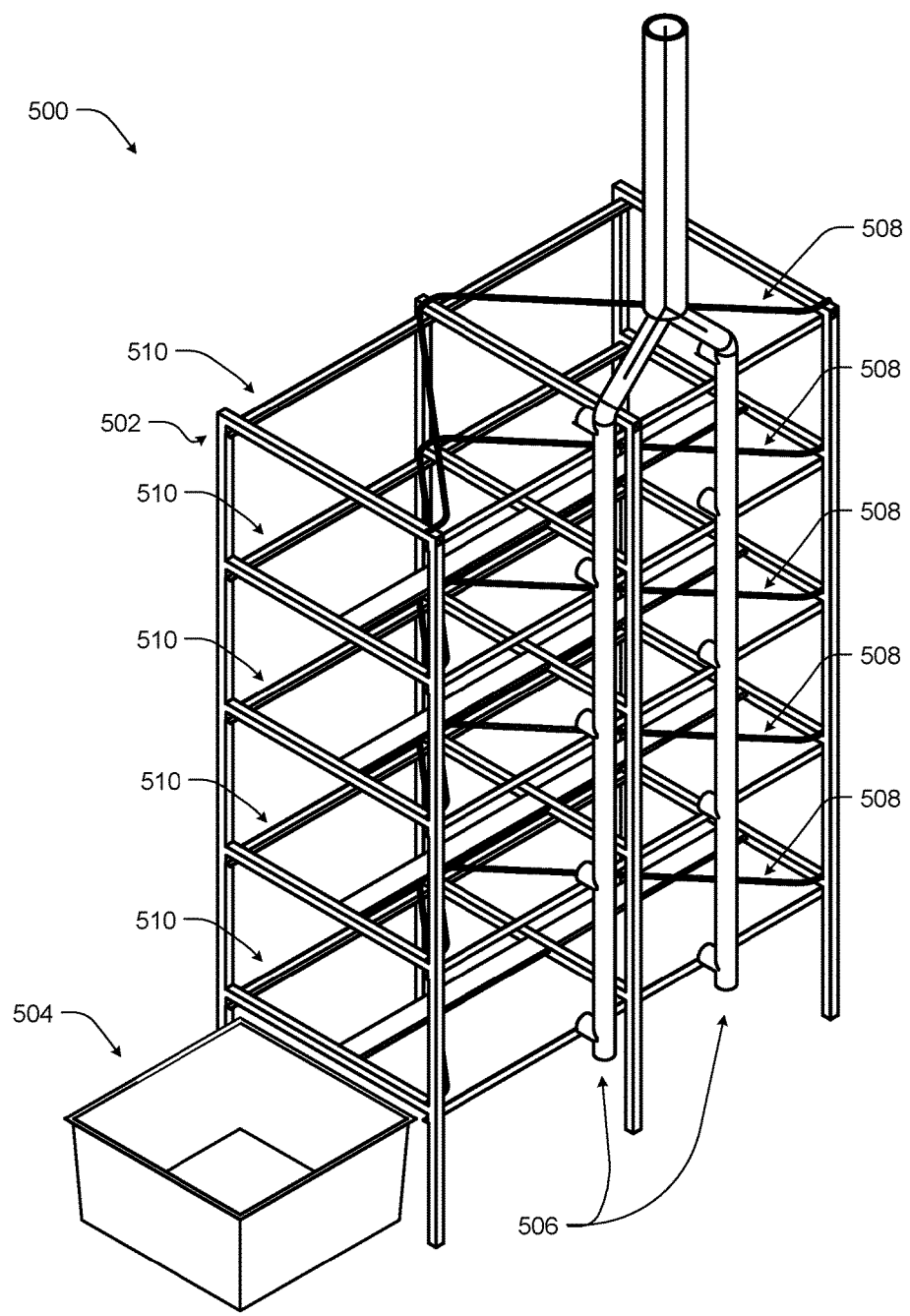
FIG. 5 illustrates an example rack system having water and feed distribution components according to some implementations.

FIG. 5 illustrates an example system 500 including a rack system 502 having feed distribution components 506 and water distribution components 508 and a habitat 504 according to some implementations. In this example, the habitats 504 may be moved and retained by the rack 502 using tracks, generally indicated by 510. For example, the lip of the habitat 504 may be placed onto the track 510 and the habitat may be moved or slid along the track 510 into position.

Figure 6:
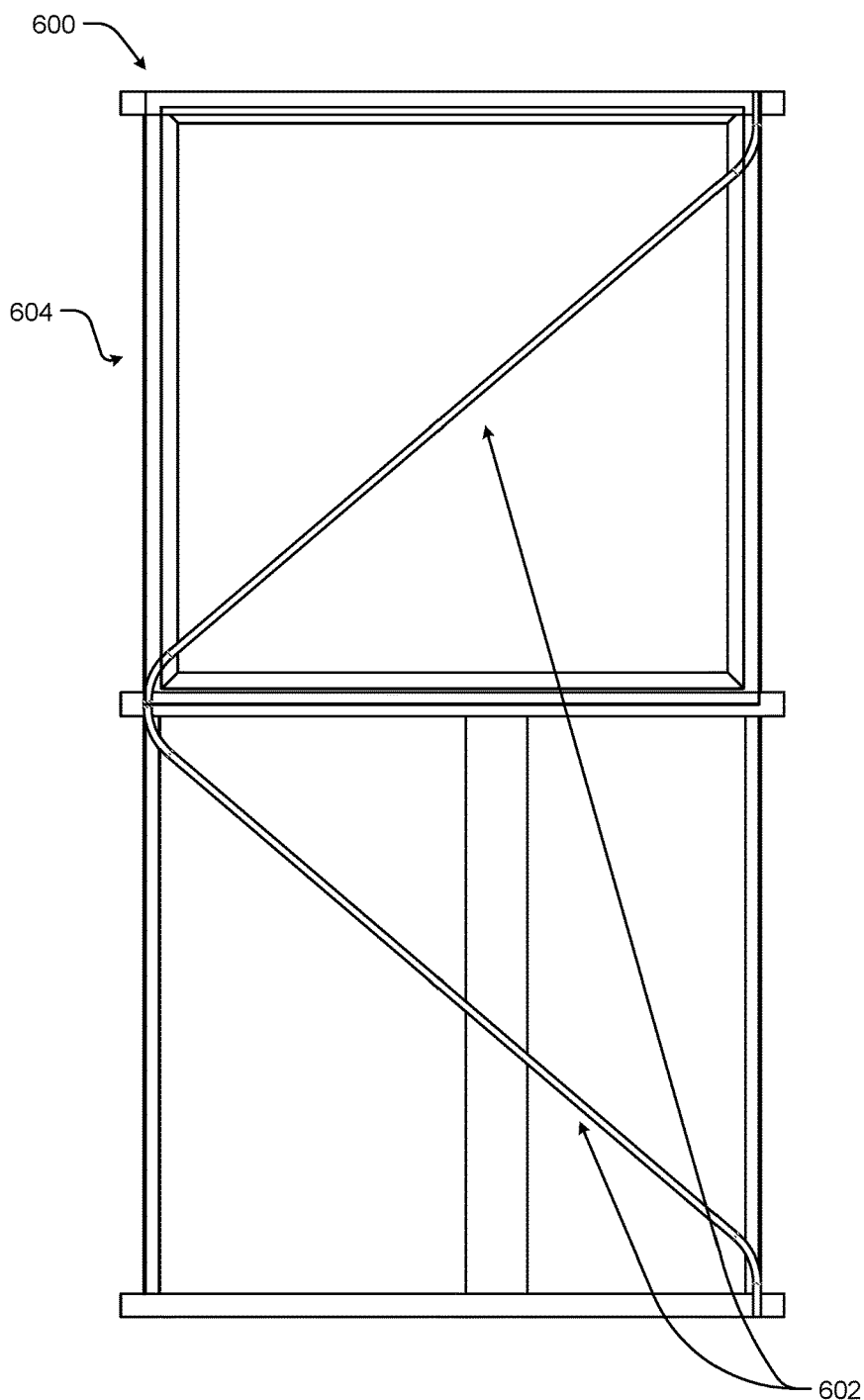
FIG. 6 illustrates an example rack system including a multi-level water distribution portion according to some implementations.

FIG. 6 illustrates an example rack system 600 including a multi-level water distribution portion 602 according to some implementations. For example, in some cases, the watering distribution portion 602 may be configured to extend up and down a column of a rack 600. For example, if the same type of insect with the same watering requirements were housed within a column of the rack system 600, the watering distribution portion 602 may provide similar watering conditions to each habitat 604.

Figure 7:
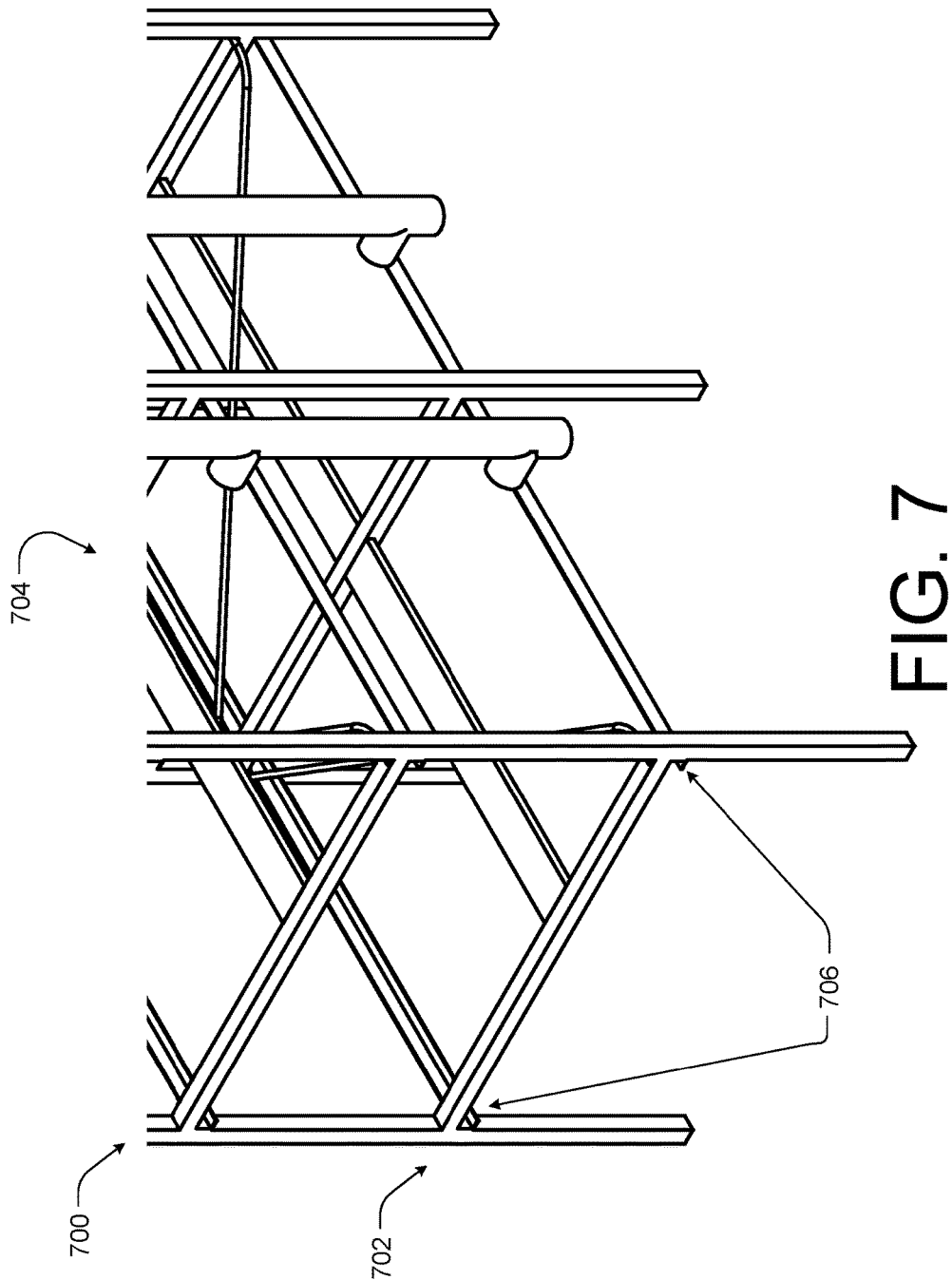
FIG. 7 illustrates an example habitat holding system associated with the rack system according to some implementations.

FIG. 7 illustrates an example habitat holding system 700 associated with the rack system 702 according to some implementations. In the illustrated example, a habitat 704 may be moved and retained by the rack 702 using tracks, generally indicated by 706. For example, the lip of the habitat 704 may be placed onto the track 706 and the habitat 704 may be moved or slid along the track 706 into position.

Figure 8:
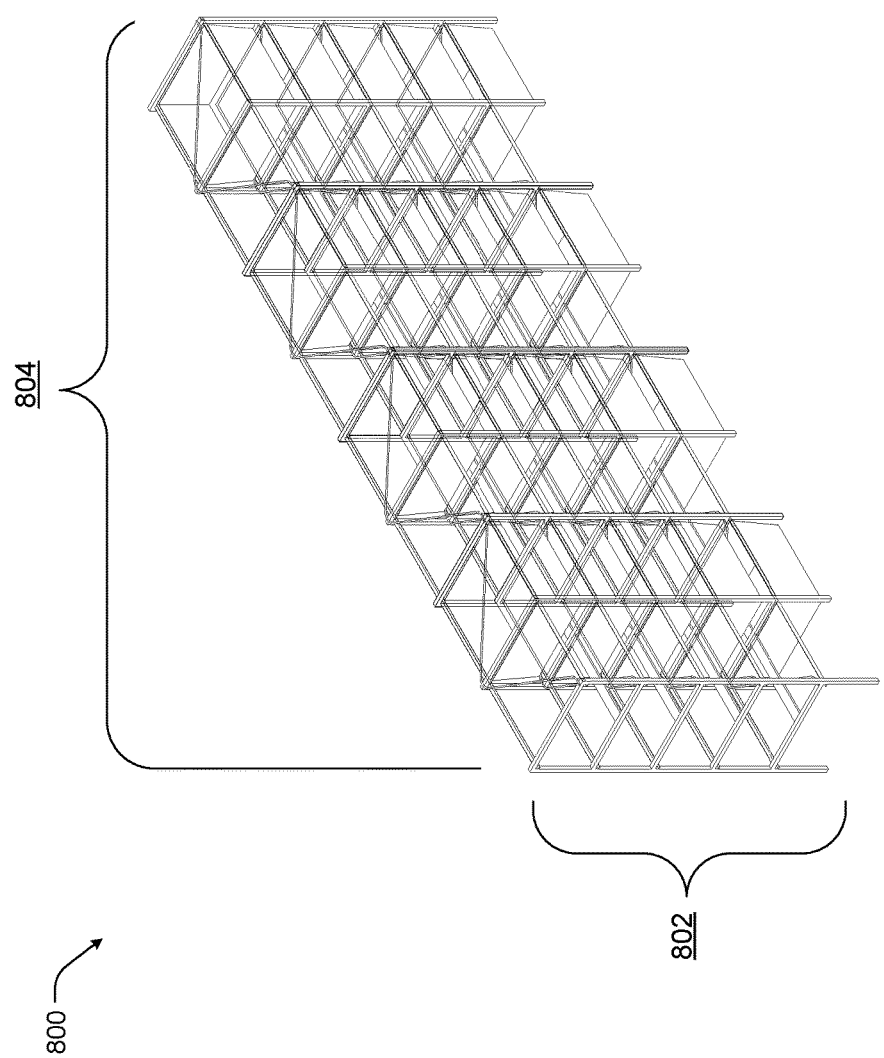
FIG. 8 illustrates an example modular rack system that may be configured with multiple rows and columns according to some implementations.

FIG. 8 illustrates an example modular rack system 800 that may be configured with multiple rows 802 and columns 804 according to some implementations. For example, the rack system 800 may be configured such that each rack may be connected or coupled to a number of adjacent racks to form rows of racks, columns of racks, or cubes of racks. In some examples, the racks 800 may be configured to include tracks moving in two directions such that the habitat may be moved in four directions along a level of the rack system 800.

Figure 9:
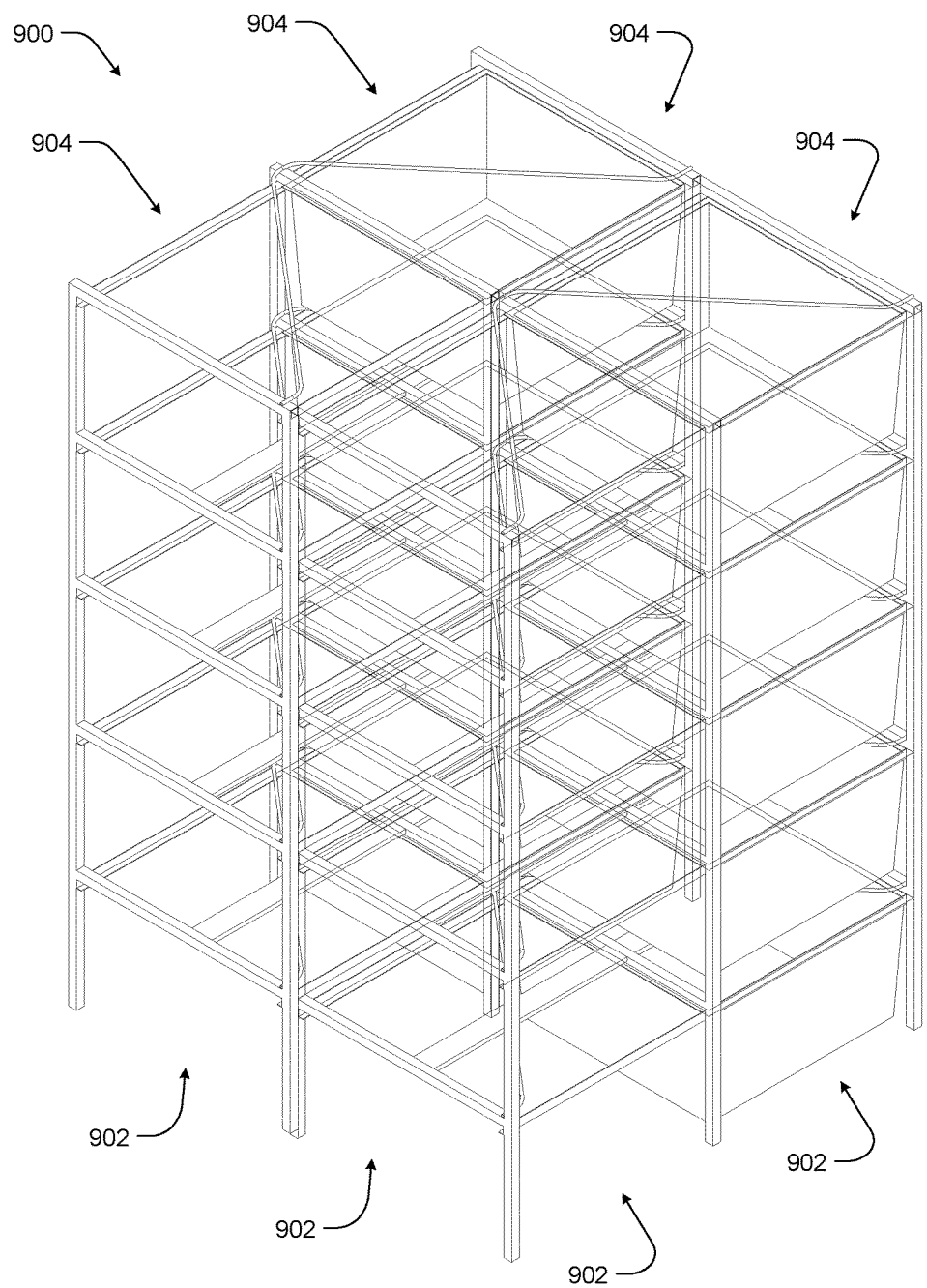
FIG. 9 illustrates an example rack system having multiple input zones and multiple output zones according to some implementations.

FIG. 9 illustrates an example rack system 900 having multiple input zones 902 and multiple output zones 904 according to some implementations. For example, as discussed above, in some implementations, the rack system 900 may be configured to allow the habitats to move in four directions within a level. In his implementation, the rack system may include two input zones 902 for loading habitats and two output zones 904 for unloading habitats.

Figure 10:
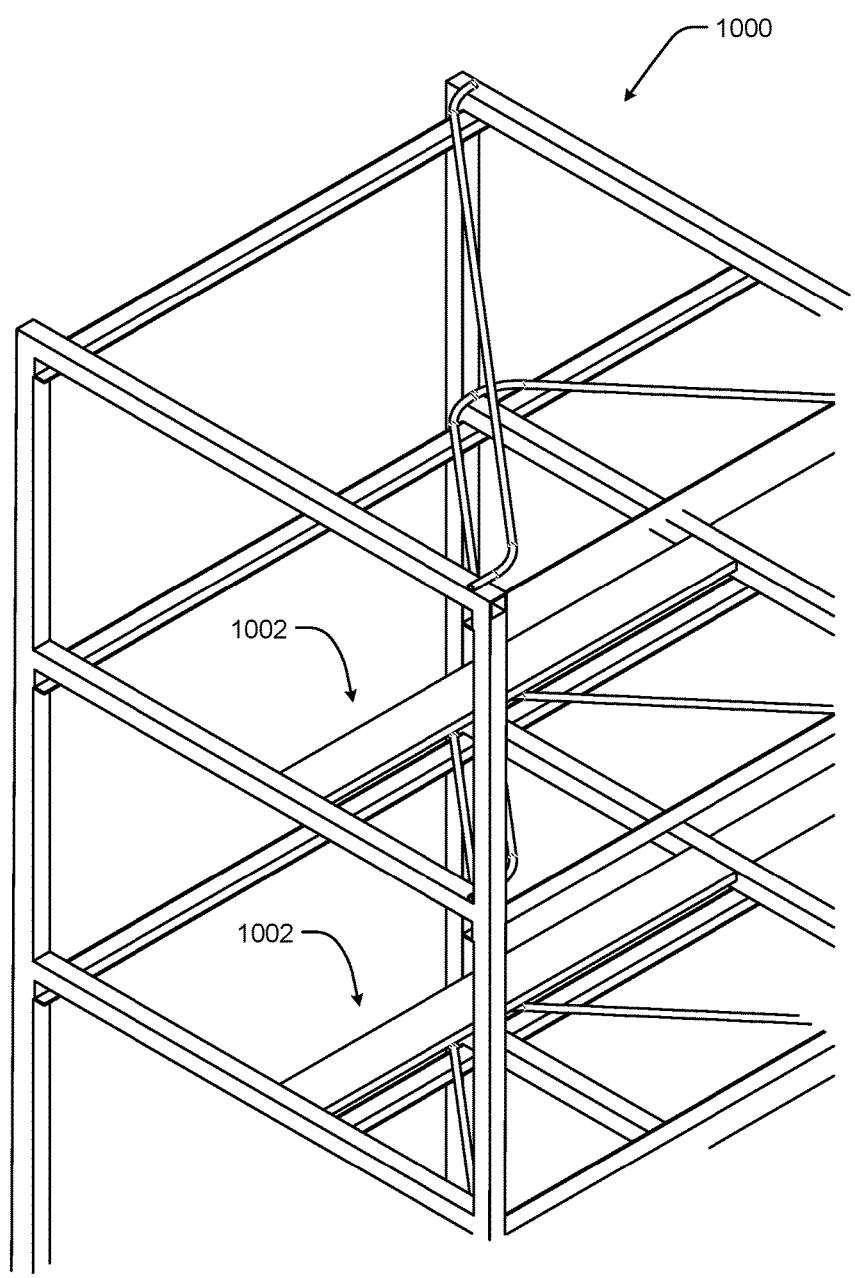
FIG. 10 illustrates an example rack system including light mounting racks or mounted lighting according to some implementations.

FIG. 10 illustrates an example rack system 1000 including light mounting racks 1002 or mounted lighting according to some implementations. For example, each location on a rack for holding a habitat may include light mounting components 1002 or lighting that may be configured for the particular needs of the insect within the associated habitat.

Figure 11:
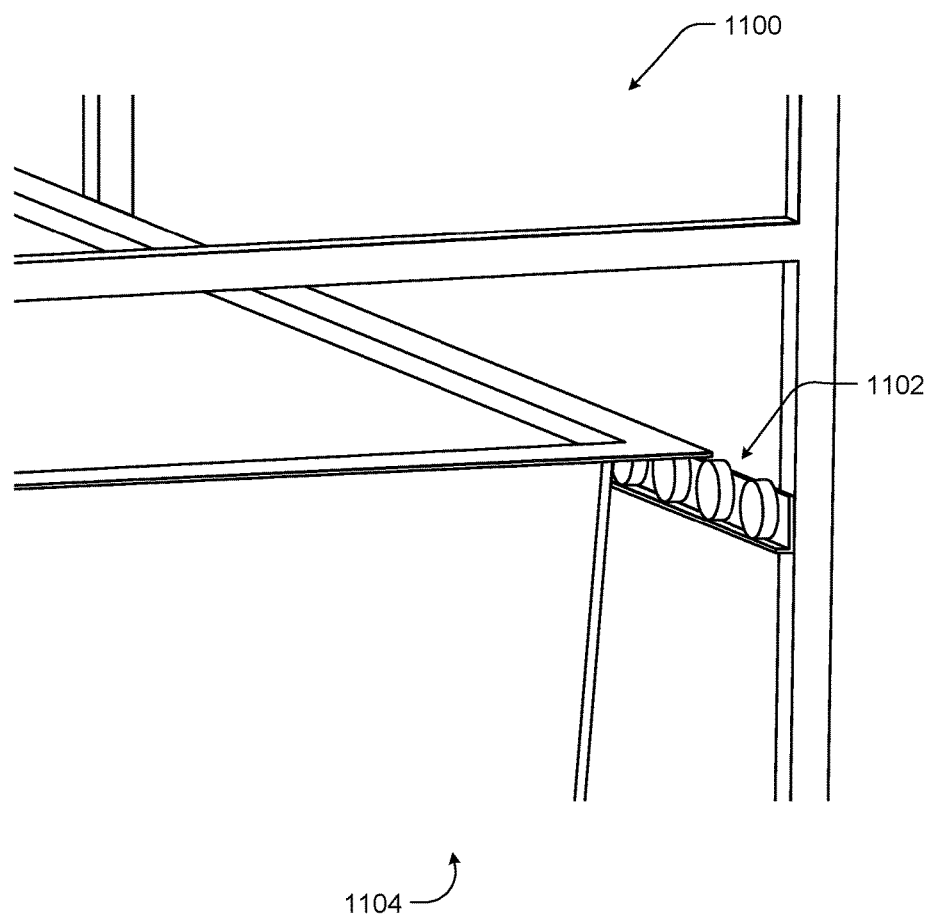
FIG. 11 illustrates an example rack system including conveying devices for assisting in moving habitats through the rack system according to some implementations.

FIG. 11 illustrates an example rack system 1100 including conveying devices 1102 for assisting in moving habitats 1104 through the rack system 1100 according to some implementations. For example, the track may include a conveying devices 1102, such as wheels, ball bearings, or other devices for easing the movement of the habitats 1104 through the rack system 1100.

Figure 12:
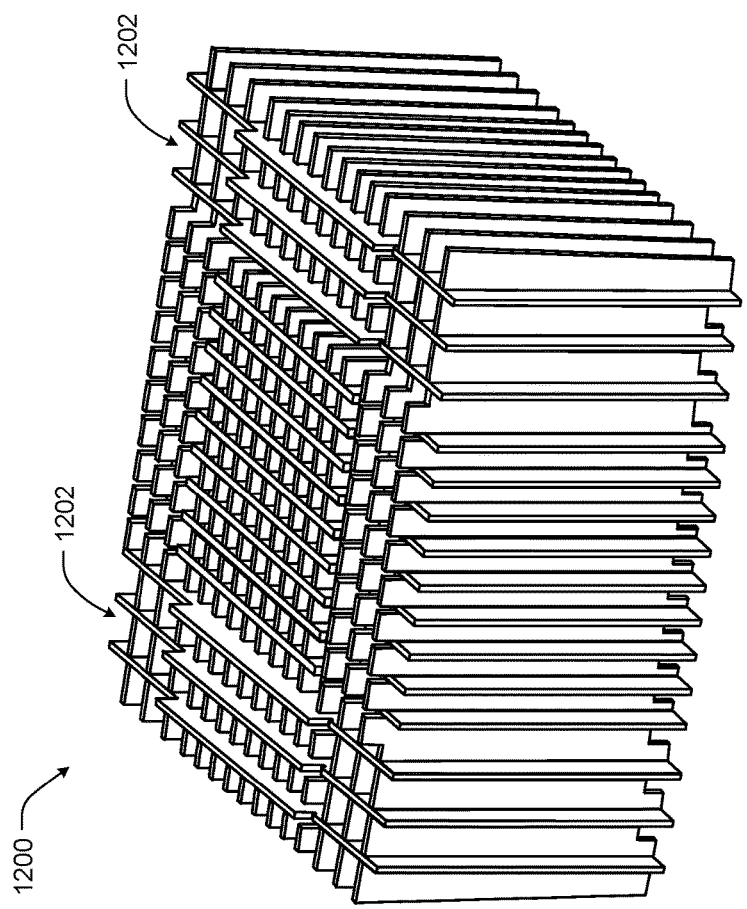
FIG. 12 illustrates an example insect habitat insert according to some implementations.

FIG. 12 illustrates an example insect habitat insert 1200 according to some implementations. The insert 1200 generally form a grid or cross-section to fill the interior space of the habitat. The insert 1200 may be formed from various materials that allow the insects to climb and/or migrate over the vertical walls of the insert 1200. For example, the surface of the insert may be rough or have a high coefficient of friction (e.g., greater than 0.5). Thus, the inserts are able to increases the surface area available to the insects and, thereby, improving overall yields per-volume. Additionally, the vertical wall of the insert helps to separate or slow the travel of the insects within the habitat which reduces the risk of pathogenic invasion, spread, and/or exposure to the insects within a single habitat. In other instances, the insert 1200 may include horizontal walls, sloping walls or angular walls depending on the type and developmental level of the insects.

The insert 1200 generally form a grid, helix or cross-section within the interior space of the habitat. In the illustrate example, the insert 1200 has opening that are of a rectangular shape formed by the interlocking of perpendicular walls. In other cases, as described below, the insert 1200 may be formed via interlocking parallel walls or in other shapes such as hexagons.

In some cases, the insert 1200 are designed to be removable from the habitat. Thus, the vertical wall design of the insert 1200 may assist with harvesting or removal of the insects from the habitat. For example, the insert 1200 may be moved over a bin and vibrated to cause the insects to fall off or detach from the vertical surfaces of the insert into the collection bins, as discussed above. In this manner, the waste remains in the habitat and the live insects disposed on the insert 1200 are deposited into the collection bins for further processing. In another example, the insert 1200 may be configured to attach or secure to the habitat, such that the inserts may be removed for cleaning or remain within the habitat when the habitat is flipped over. In some designs, the insert 1200 may include notches or depressed regions 1202 in the top surface to receive objects at a predetermined location. For example, the notches 1202 may be configured to receive feeding or watering apparatuses or trays that are reachable by the insects in a manner that prevents the apparatuses from moving or sliding which may result in damage or death to the insects. In one particular example, a water tray may be configured to fit into the depressed regions 1202 and to receive water from the water delivery system when correctly placed within the depressed region 1202. The type or configuration of the water tray may vary depending on the life stage of the insects within the habitat. For example, for smaller insects, which are easily drowned, the water tray may include an area having fibrous or porous material, such as peat moss, coconut fiber, etc., that may absorb water on the tray. The insects may access the water within the porous material without the risk of drowning. In other examples, as the insects mature, the insects may be unable to obtain sufficient water from the porous material. In these examples, the water tray may include a perforated float that allows the insects to access the water within the tray without being able to fall into and drown, as the insects are predisposed to do in standing water. In another particular example, one or more of the depressed regions 1202 maybe configured to receive a food tray for distributing feed to the insects within the habitat.

In some cases, the inserts 1200 may include a first horizontal plane and a second horizontal plane beneath the first horizontal plane. Some of the interior walls may extend to the first horizontal plans along the length of the wall, while other interior walls may include a first portion extending to the first horizontal plane and a second and/or third portion extending to the second horizontal plane. In this manner the insert 1200 may include areas of differing heights or the depressed regions 1202 for receiving the water and feed trays. The insert 1200 may also include perforations along the interior walls to increase air flow and insect mobility throughout the entire volume and allow the insects to more easily reach the watering and feeding apparatus placed within the habitat. In some specific examples, the insert 1200 may be configured to provide an electric charge which attracts and holds the insects to the walls of the insert 1200 prior to removal of the insert 1200 from the habitat. In another example, the walls of the insert 1200 may be configured to release a chemical compound to attract the insects to the walls or a chemical additive that causes the insects to stick or adhere to the walls during a period of time prior to and during removal of the insert 1200. For instance, the walls of the insert 1200 may include pores that allow chemicals stored or injected into the walls to seep out during the removal process.

Figure 13:
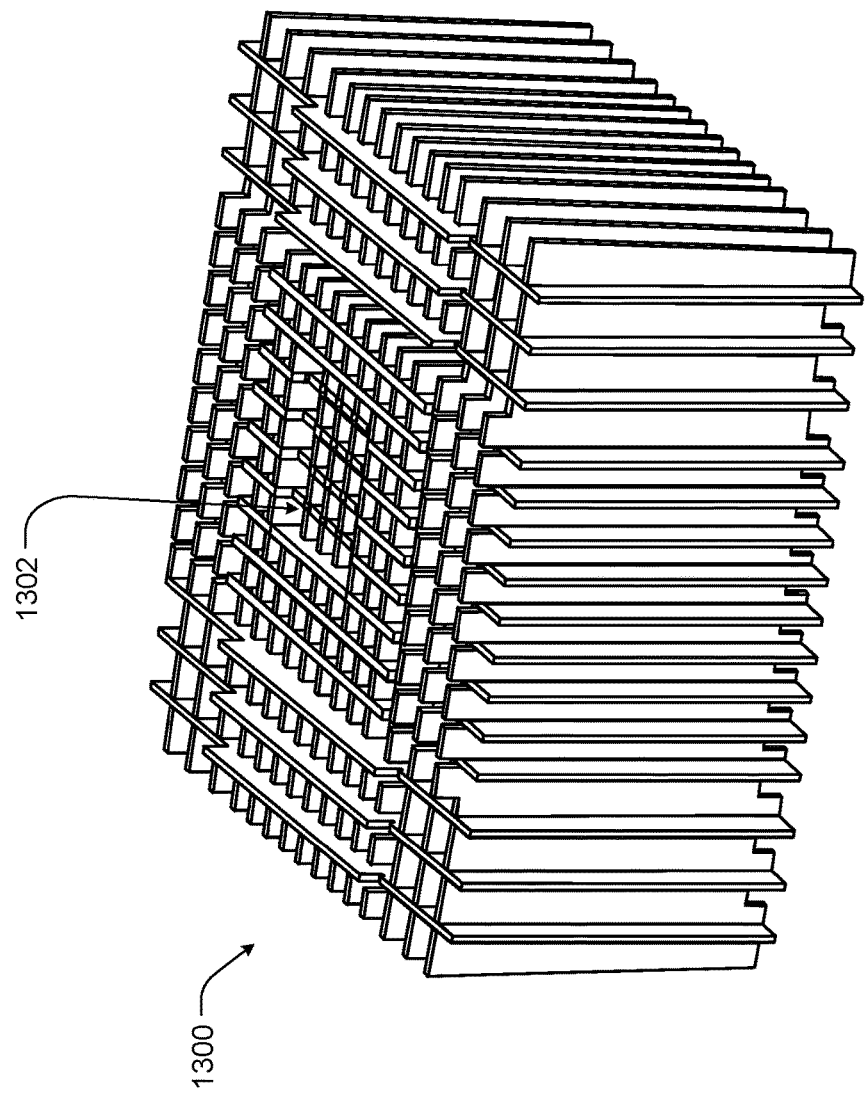
FIG. 13 illustrates an example insect habitat insert including designated feed and water stations according to some implementations.

FIG. 13 illustrates an example insect habitat insert 1300 including designated feed and water stations according to some implementations. As described above, the insert 1300 may include notches or depressed regions 1302 in the top surface to receive objects at a predetermined location. For example, the notches 1302 may be configured to receive feeding or watering apparatuses that are reachable by the insects in a manner that prevents the apparatuses from moving or sliding which may result in damage or death to the insects.

In the previous example of FIG. 12, the insert 1200 included depressed regions 1202 in the corners or along the exterior of the insert 1200. However, in the current example, the depressed region 1302 is located along the center of the insert 1300. Thus, it should be understood by one skilled in the art that the depressed region 1302 may be configured at various locations along the top surface of the insert 1300 and that inserts having different depressed regions may be utilized for different insects, different feeding and/or watering arrangements, as well as for different life stages of a particular type of insect, such as a cricket.

Figure 14:
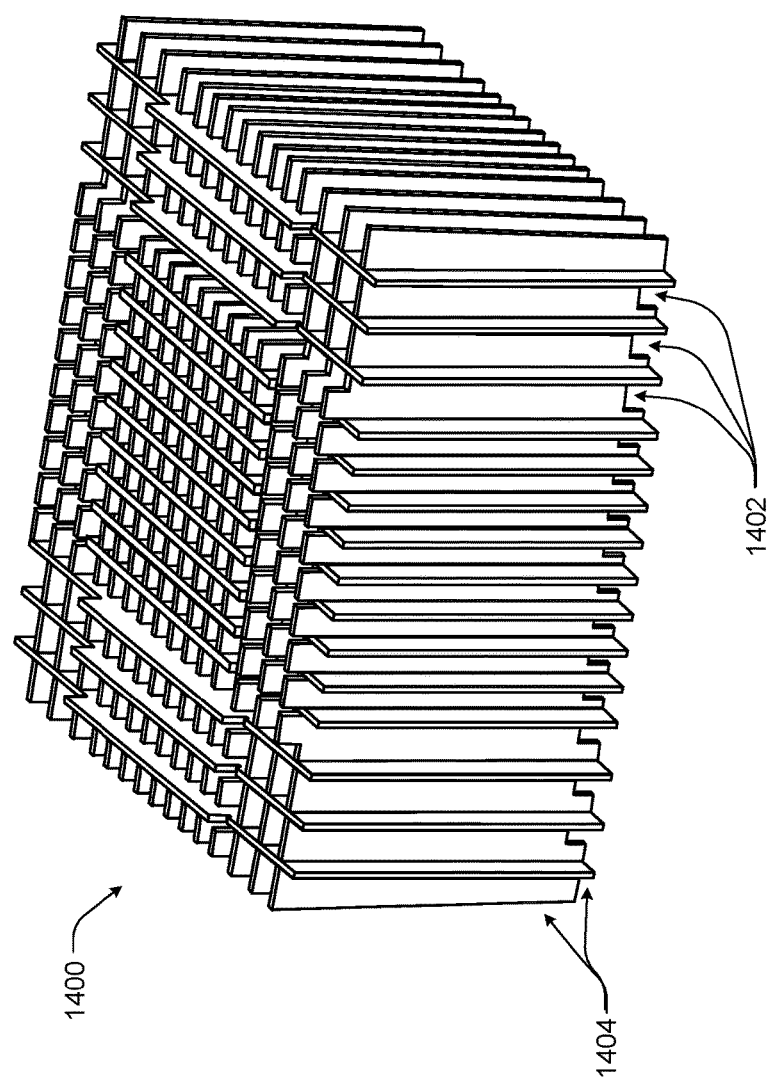
FIG. 14 illustrates an example insect habitat insert having perforations for improved insect mobility within the habitat according to some implementations.

FIG. 14 illustrates an example insect habitat insert 1400 having perforations 1402 for improved insect mobility within the habitat according to some implementations. In some cases, the insert 1400 may also include perforations 1404 along the interior walls to increase air flow and insect mobility throughout the entire volume and allow the insects to more easily reach the watering and feeding apparatus or trays placed within the habitat. Additionally, the insert 1400 may include vertical walls 1404 to assist with harvesting of the insects when the insert is removed from the habitat. For example, the inserts may be removed from the habitat, positioned over collection bins, and vibrated to cause the insects to fall off of or detach from the vertical surfaces of the insert.

Figure 15:
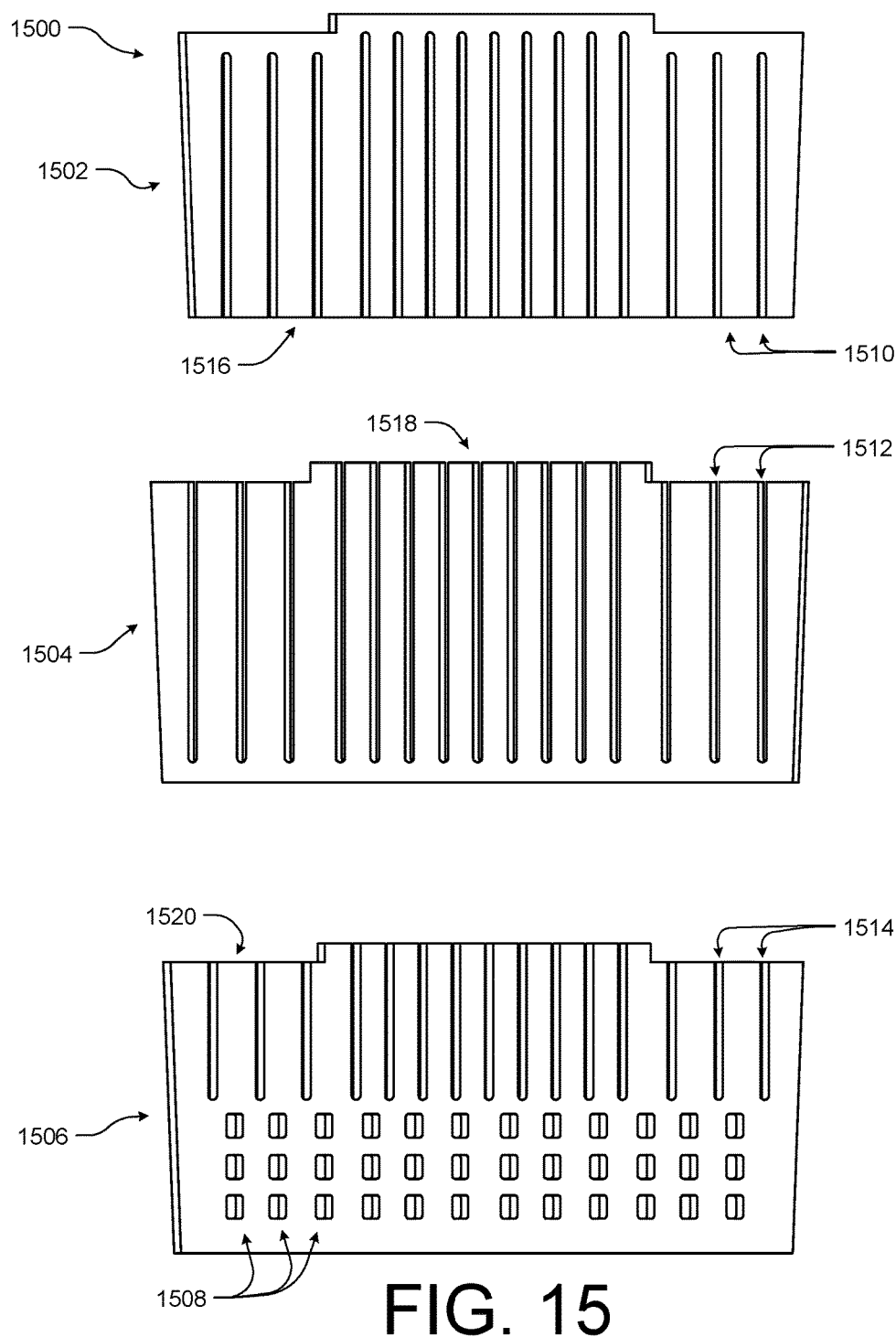
FIG. 15 illustrates an example vertical walls or members of an insect habitat insert prior to assembly according to some implementations.

FIG. 15 illustrates an example vertical walls or members 1500 of an insect habitat insert prior to assembly according to some implementations. In this example, the insert may be formed by interlocking vertical walls or members 1500 via locking channels, generally indicated by 1510, 1512, and 1514. For instance, the insert includes a plurality of vertical walls or members 1500 may include a plurality of top members 1502 and a plurality of bottom members, such as members 1504 and members 1506. In the illustrated example, the locking channels 1510, 1512, and 1514 may mate in a manner to cause the plurality of top members 1502 to run in a perpendicular direction to the plurality of bottom members 1504. In other words, the intersection of the plurality of top members 1502 and the plurality of bottom members 1504 and 1506 may from a grid having ninety degree 90° angles. Thus, in the current illustration, the plurality of top members 1502 and the plurality of bottom members 1504 and 1506 form a rectangular grid extending upwards form the floor of a habitat in which the insert is placed to increase the overall surface area of the habitat and to, thereby, increase the overall yield of insects raised within the same cubic space.

As discussed above, the top members 1502 and the bottom members 1504 and 1506 may be configured to interlock via locking channels 1510 and 1512 to form a grid or cross-section that increases the surface area within a habitat. Each of the locking channels 1510 may be gaps or slits having an opening on a bottom surface 1514 of the top members and extend upward from the bottom surface 1514 into the body of the top member 1502. In the current example, the locking channels 1510 extend upward for approximately 90% of the height of the body of the top members 1502. However, in other examples, the locking channels 1510 may extend upward from between 35% and 95% of the height of the body of the top members 1502.

Each of the locking channels 1512 of the bottom members 1504 has an opening on the top surface 1518 of the bottom members 1504 and extends downwards into the body of the bottom members 1504. In the current example, the locking channels 1512 extend downwards for approximability 90% of the height of the body of the bottom members 1504. However, in other examples, the locking channels 1512 may extend downward from between 35% and 95% of the height of the body of the bottom members 1504.

Similarly, the locking channels 1514 of the bottom members 1506 also have an opening on the top surface 1520 of the bottom members 1506 and extend downward into the body of the bottom members 1506. In the current example, the openings extend downward approximate 50% of the height of the body of the bottom member 1506 or, in other words, are confined to the top portion or top half of the bottom member 1506. In other examples, the openings extend downward approximate 40% of the height of the body of the bottom member 1506, 35% of the height of the body of the bottom member 1506, or 30% of the height of the body of the bottom member 1506.

In the illustrated example, the locking channels 1514 are confined to the top portion of the bottom member 1506, as the bottom members 1506 include perforations 1508 to improve airflow and allow the insects to move between different areas of the habitat. For example, the perforations 1508 may be openings within the walls of the members 1502, 1504, and/or 1506 to allow insects to move between the walls of the habitat insert and to prevent the insects from being trapped without access to water or feed. In this example, the bottom member 1506 includes perforations 1508 but it should be understood that the top members 1502 may also include perforations and that the perforations 1508 may not be contained to the lower portion of the bottom member 1506. For example, the perforations 1508 may be interspaced between the locking channels 1514 and run the entire height and/or length of the members 1502, 1504, and/or 1506.

Figure 16:
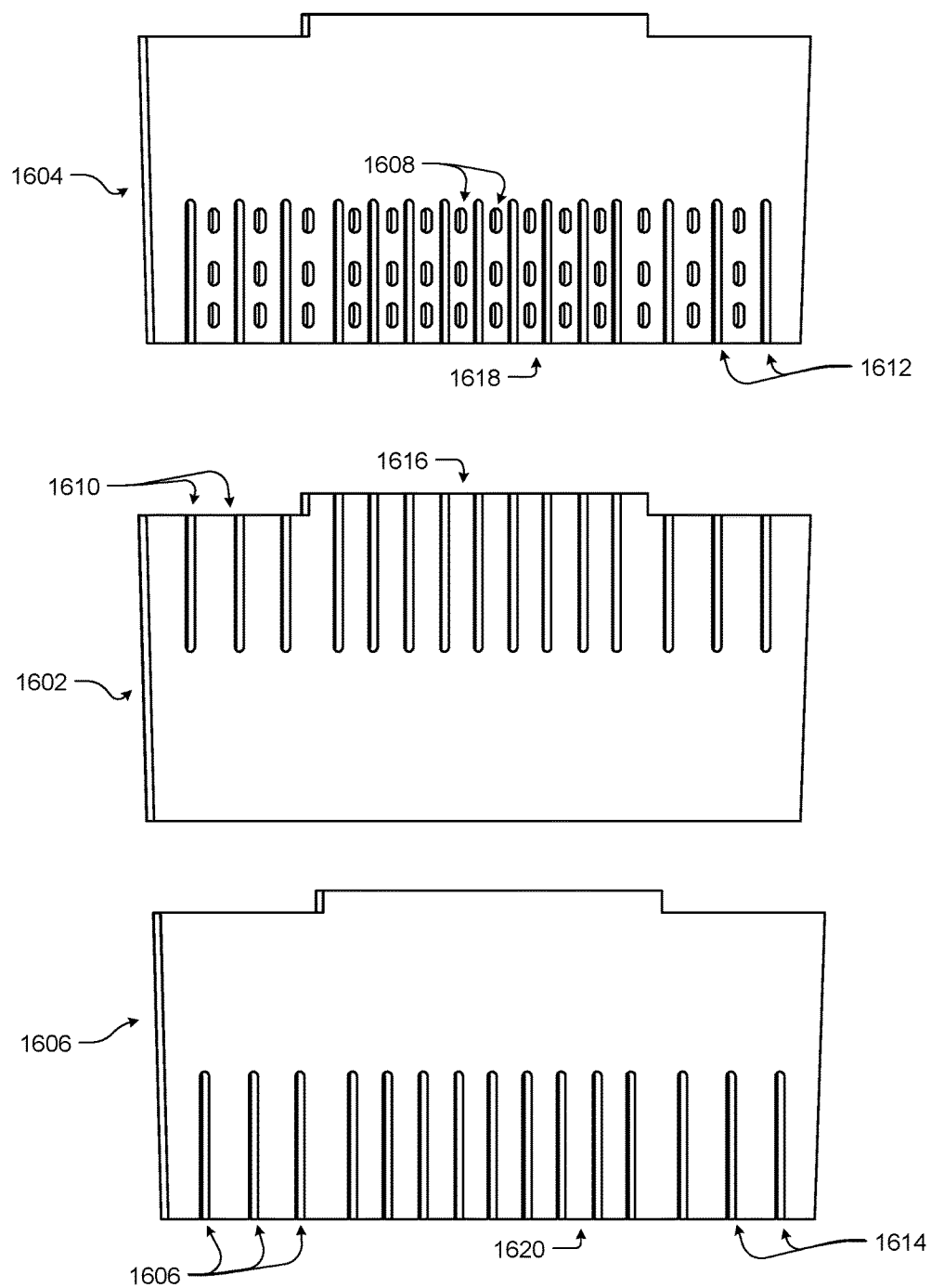
FIG. 16 illustrates another example vertical walls or members of an insect habitat insert prior to assembly according to some implementations.

FIG. 16. illustrates another example vertical walls or members 1600 of an insect habitat insert prior to assembly according to some implementations. In this example, the insert may include a plurality of bottom members 1602 as well as a plurality of top members 1604 and 1606. In the current example, the bottom members 1502 includes locking channels 1610, the top members 1604 include locking channels 1612, and the top members 1606 include locking channels 1614. As discussed above, the top members 1604 and 1606 may be configured to interlock with the bottom members 1602 via the locking channels 1610, 1612, and/or 1614 to form a grid or cross-section that increases the surface area within a habitat.

In the current example, each of the locking channels 1610 may be gaps or slits having an opening on a top surface 1616 of the top members and extending downward from the top surface 1616 into the body of the bottom member 1602. In the current example, the locking channels 1610 extend downward for approximability 50% of the height of the body of the bottom members 1602. However, in other examples, the locking channels 1610 may extend downward from between 35% and 95% of the height of the body of the bottom members 1602.

Each of the locking channels 1612 of the top members 1604 has an opening on the bottom surface 1618 of the top members 1604 and extends upward into the body of the top members 1604. In the current example, the locking channels 1612 extend upward for approximability 50% of the height of the body of the top members 1604. However, in other examples, the locking channels 1612 may extend upward from between 35% and 95% of the height of the body of the top members 1604. Similarly, the locking channels 1614 of the top members 1606 also have an opening on the bottom surface 1620 of the top members 1606 and extend upward into the body of the top members 1606. In the current example, the extend upward approximate 50% of the height of the body of the top member 1606. In other examples, the extend upward approximate 40% of the height of the body of the top member 1606, 35% of the height of the body of the top member 1606, or 30% of the height of the body of the top member 1606. In some cases, the locking channels 1614 may extend upward from between 35% and 95% of the height of the body of the top members 1604. In the current example, the locking channels 1610, 1612, and/or 1614 are shown as slits or rectangular openings within the body of the respective member 1602, 1604, and/or 1606, however, it should be understood that the shape of the locking channels 1610, 1612, and/or 1614 may vary.

In the current example, the top member 1604 includes perforations 1608 to improve airflow and allow the insects to move between different areas of the insert or habitat. In this example, the top member 1504 includes perforations 1608 but it should be understood that the bottom member 1602 may include perforations and that the perforations, such as bottom member 1506 of FIG. 5. For instance, in one particular implementation, the top member 1604 may be used in conjunction with the bottom member 1504 of FIG. 5 to form an insect having perforations to move left and right as well as forward and backward through the insert within a habitat. Additionally it should be understood that, the perforations 1608 may not be contaminated to the lower portion of the top member 1604. For example, the perforations 1608 may be interspaced between the locking channels 1612 and run the entire height and/or length of the members 1604.

In some examples, the perforations 1608 may be approximately 45 millimeters (mm) high and approximately 10 mm wide. In other examples, a height and width of each of the perforations 1608 may vary between 5 mm and 80 mm. In one particular example, the perforations 1608 may be approximately 45 mm by 45 mm. Additionally, in the current example, the perforations 1608 are uniform but in some implementations, the size (e.g., height or width) of the perforations 1608 may vary between individual perforations.

Figure 17:
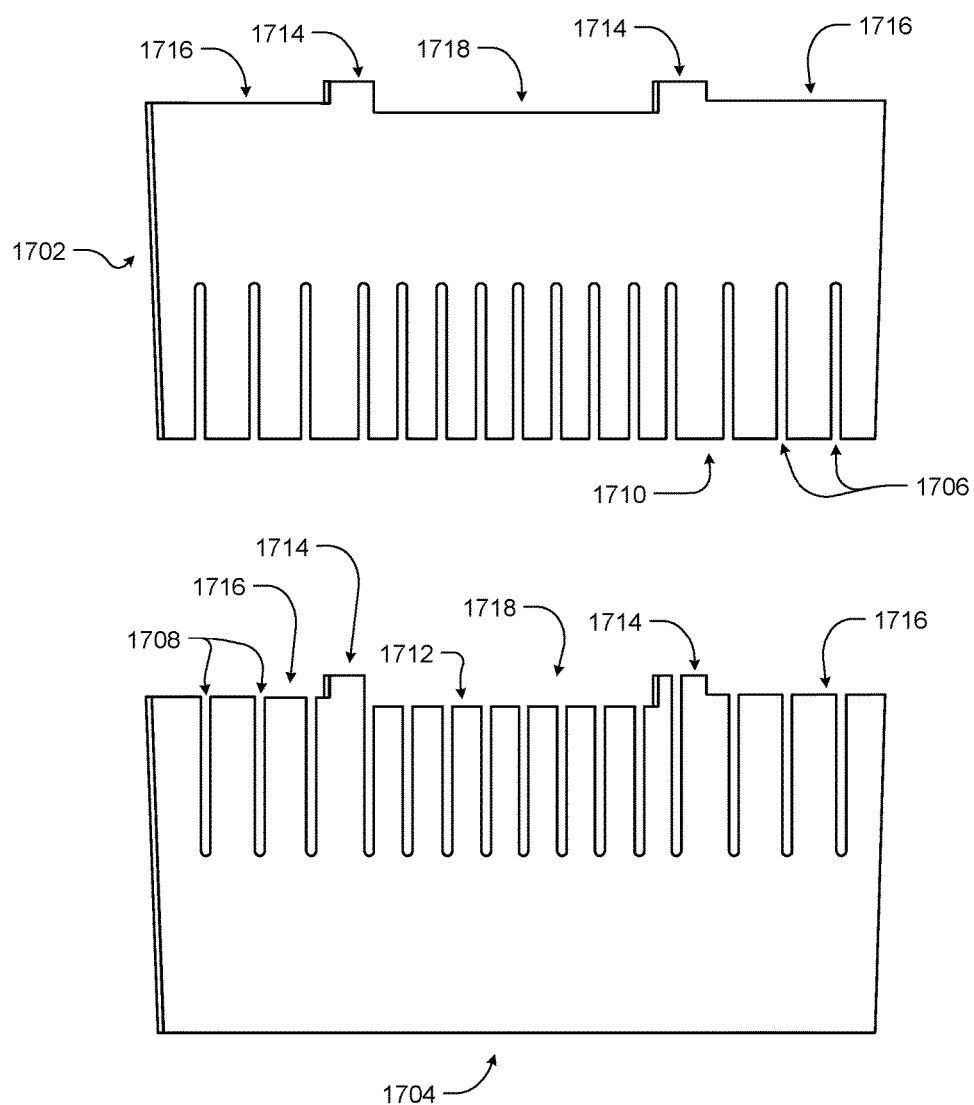
FIG. 17 illustrates yet another example vertical walls or members of an insect habitat insert prior to assembly according to some implementations.

FIG. 17 illustrates yet another example vertical walls or members 1700 of an insect habitat insert prior to assembly according to some implementations. In this example, the insert 1700 may include a plurality of top members 1702 and a plurality of bottom members 1704. As discussed above, the top members 1702 and the bottom members 1704 may be configured to interlock via locking channels or components, such as locking channels 1706 and 1708. In the illustrated example, the locking channels 1706 have an opening along a bottom surface 1710 of the top member 1702 and extend upward approximately 50% of the height of the body of the top member 1702. Likewise, the locking channels 1708 have an opening along a top surface 1712 of the bottom member 1704 and extend downward approximately 50% of the height of the body of the bottom member 1704. As discussed above, when interlocked the top members 1702 and the bottom members 1704 are coupled via the locking channels 1706 and 1708, the top members 1702 and the bottom members 1704 forms a grid or cross-sectional insert configured to be placed within a habitat for the cultivation of insects, such as crickets.

In the current example, the top members 1702 and the bottom members 1704 include portions 1714 at a first height, portions 1716 at a second height below the first height, and portions 1718 at a third height below the second height to define areas along a top surface of the insert formed via the top members 1702 and the bottom members 1704. For example, the portions 1716 may be configure to receive feed trays and the portion 1718 may be configured to receive water trays that may be replaced or resupplied via a device or operator of a facility housing the insect habitats. By including the various heights along a top surface of the insert formed by the top members 1702 and the bottom members 1704, the feed and water trays may be maintained in positions without risk of movement that could harm or damage the insects while allowing easy access to the feed/water delivery device or operator.

The examples of FIGS. 15-17 illustrate various members, it should be understood that the various members of each of the FIGS. 15-17 may be utilized in any combination to form various different configurations of inserts for use within an insect habitat.

Figure 18:
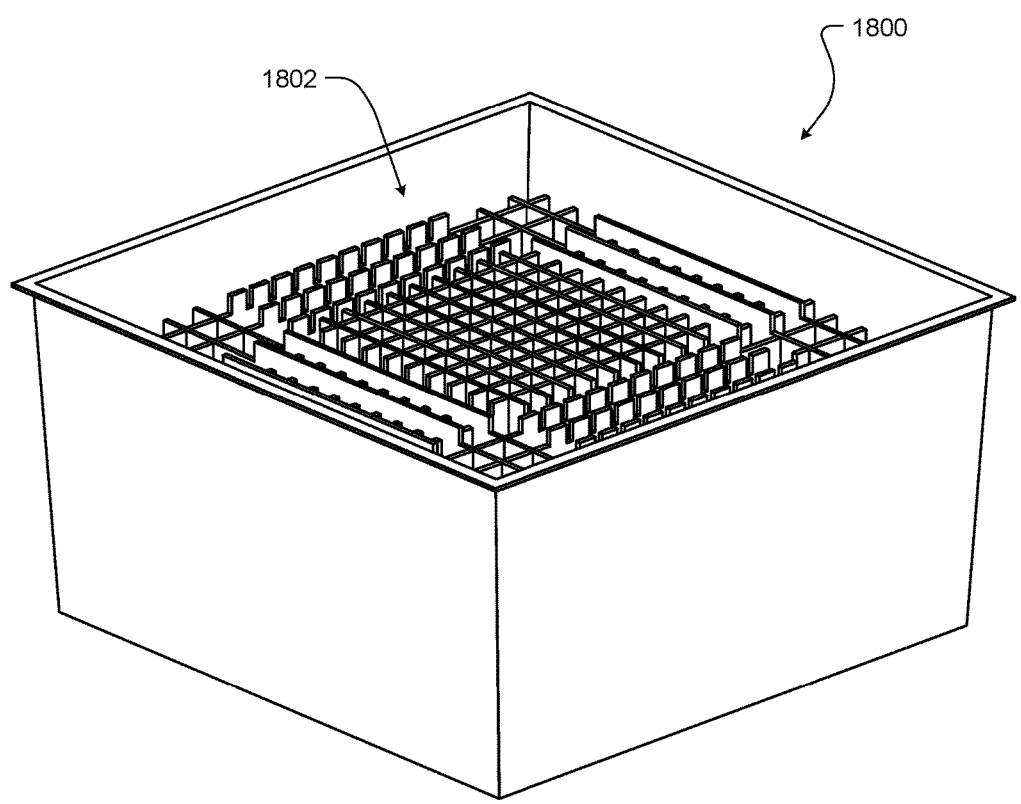
FIG. 18 illustrates an example habitat including an insect habitat insert according to some implementations.

FIG. 18 illustrates an example habitat 1800 including an insect habitat insert 1802 according to some implementations. In some cases, the inserts 1802 are designed to be removable from the habitat 1800. Thus, the vertical wall or members of the inserts 1802 may assist with harvesting of the insects when the insert 1802 is removed from the habitat 1800. For example, the inserts 1802 may be moved over a bin, another habitat, or the habitat 1800 and vibrated to cause the insects to fall off of or detach from the vertical surfaces of the insert 1802.

In the current example, the habitat 1800 may vary in height from approximately 8 inches to a height of approximately 3 feet. In some cases, the habitat 1800 may be less than 2 feet. In the various implementations, the insert 1802 when assembled may range from in height from approximately 2 inches to 32 inches. In some cases, the height of the insert 1802 may be greater than or equal to 3 inches and less than or equal to 20 inches. In some cases, the height of the insert 1802 may be based on the eight of the habitat 1800. For example, the height of the insert 1802 may be approximately 5 inches less than the height of the habitat 1800. In other cases, the height of the insert 1802 may be between approximately 3 inches and 7 inches less than the height of the habitat 1800.

In the illustrated examples of FIGS. 12-18, the inserts include vertical walls or members. However, the inserts may be designed to include horizontal walls with or without vertical perforations. In other cases, the insert may include sloping walls or angular walls depending on the type and developmental level of the insects.

Figure 19:
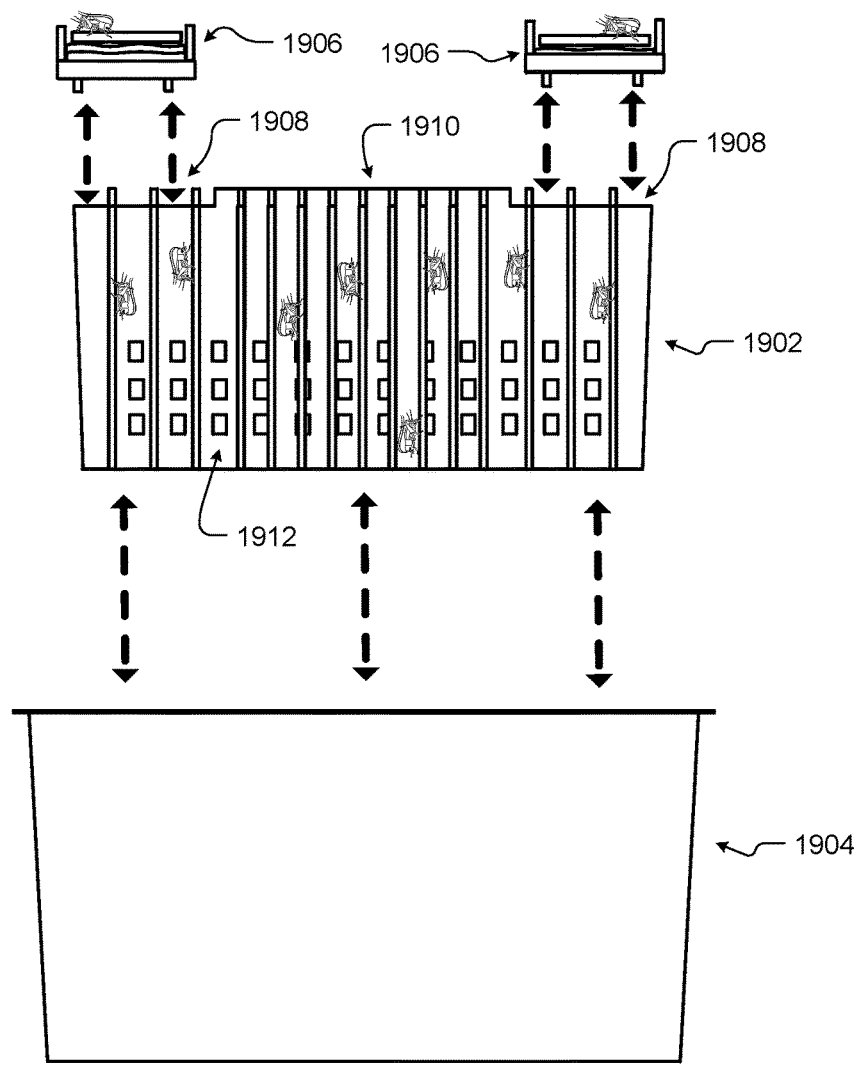
FIG. 19 illustrates an example of an insert removed from a habitat according to some implementations.

FIG. 19 illustrates an example of an insert 1902 removed from a habitat 1904 according to some implementations. The insert 1902 may be included in the habitat 1904 to increase the overall total surface area within the same volume previously contained within the habitat 1904, as the increase in surface area results in a corresponding increase in the insects that may be cultivated within the same volume of space. In the illustrated example, the insert 1902 may generally form a grid, helix or cross-section within the interior space of the habitat 1904.

As shown in the illustrated example, the insert 1902 may be removable from the habitat 1904 and include vertical walls or members that allow the insert 1902 to be shaken to be dislodged or removed from the habitat 1904 during harvesting in a more efficient manner. For example, the insert 1902 may be moved over a collection bin and vibrated to cause the insects to fall off of or detach from the surfaces of the insert 1902.

In the current example, the insert 1902 is configured to receive feed and/or water tray 1906 shown removed from the insert 1902. For instance, the trays 1906 may be removable for cleaning prior to or following the harvesting of the insects. In some cases, the trays 1906 may be positioned at predetermined locations within the habitat 1904, for instance, by including a depressed regions 1908 on the top surface of the insert 1902, as discussed above. Thus, the trays 1906 may be easily positioned at a location within the habitat 1904 to receive feed or water from the delivery system or operator. In the illustrated example, two trays 1906 are shown. However, it should be understood that the habitat 1904 and/or the insert 1902 may be configured to hold any number of trays. In some cases, the height of the insert 1902 at the depressed regions 1908 may be less than an overall height of the insert 1902 at other regions, generally indicated by 1910. For example, the height of the depressed regions 1908 may be one inch or less than the height of other regions 1910. In other cases, the difference in height between the depressed regions 1908 and the other regions 1910 may be between half an inch and four inches.

In some examples, the insert 1902, the habitat 1904, and/or the trays 1906 may be configured with various sensors or switches, such as weight sensors, temperature sensors moisture sensors, float sensors, contact sensors, proximity sensors, water gauges, pH monitors, image components, etc., that may collect data related to the water, feed, health of the insects, movement of the insects, etc. In some instances, the data collected by the sensors may be provided to a monitoring system or operator of the facility including the habitat 1904. In some cases, in lieu of or in addition to the sensors, image components may be positioned to capture image data associated with the water, feed, health of the insects, movement of the insects, etc.

The insert 1902 may also include perforations 1912 along the interior walls or members to increase airflow and insect mobility throughout the entire volume of the habitat 1904. For example, the perforations 1912 may be approximately 45 millimeters (mm) high and approximately 10 mm wide. In other examples, a height and width of each of the perforations 1912 may vary between 5 mm and 80 mm. In one particular example, the perforations 1912 may be approximately 45 mm by 45 mm. Additionally, in the current example, the perforations 1912 are uniform but in some implementations, the size (e.g., height or width) of the perforations 1912 may vary between individual perforations.

Figure 20:
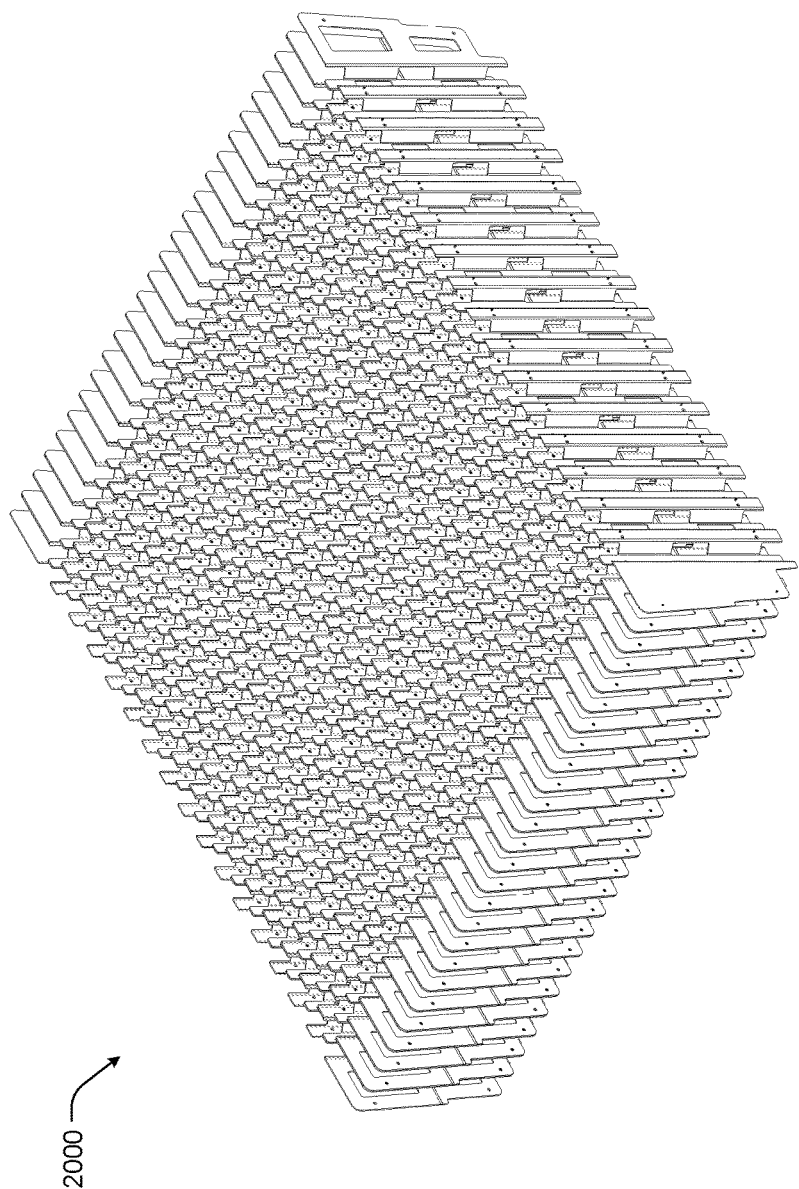
FIG. 20 illustrates an example insect habitat insert according to some implementations.

FIG. 20 illustrates an example insect habitat insert 2000 according to some implementations. In the illustrated example, the insert 2000 generally form a hexagonal gird and may be formed from various materials that allow the insects to climb and/or migrate over the vertical walls of the insert 2000. For example, the surface of the insert may be rough or have a high coefficient of friction (e.g., greater than 0.5). Thus, the inserts are able to increases the surface area available to the insects and, thereby, improving overall yields per-volume. Additionally, the vertical wall of the insert helps to separate or slow the travel of the insects within the habitat which reduces the risk of pathogenic invasion, spread, and/or exposure to the insects within a single habitat. In other instances, the insert 1200 may include horizontal walls, sloping walls or angular walls depending on the type and developmental level of the insects.

In the current example, unlike the examples above, the insert 2000 is formed from substantially identical vertical walls arranged in a parallel fashion. Thus, the vertical walls used to form the insert 2000 may be stamped, molded, or otherwise manufactured using a single die, mold, press, or casing, thereby reducing the overall costs associated with manufacturing the insert 2000. Additionally, by utilizing substantially identical vertical walls that snap or otherwise secure to each other, the insert 2000 may be formed in any length or by any number of vertical walls.

In the current example, the insert 2000 is shown removed from a habitat. Thus, as discussed above, the vertical wall design of the insert 2000 may assist with harvesting or removal of the insects from the habitat. For example, the insert 2000 may be moved over a bin and vibrated to cause the insects to fall off or detach from the vertical surfaces of the insert into the collection bins, as discussed above. In this manner, the waste remains in the habitat and the live insects disposed on the insert 2000 are deposited into the collection bins for further processing.

Figure 21:
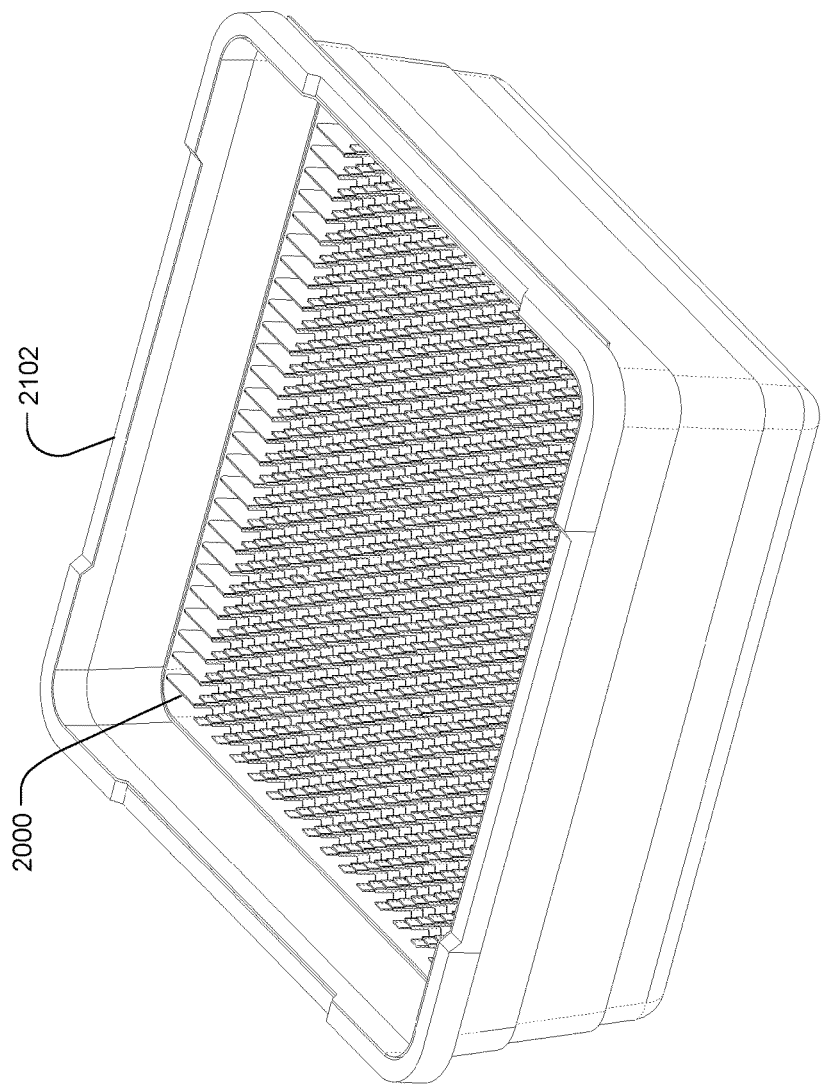
FIG. 21 illustrates an example view of the insert of FIG. 20 within a habitat according to some implementations.

FIG. 21 illustrates an example view of the insert 2000 of FIG. 20 within a habitat 2102 according to some implementations. In the current example, the insert 2000 is less than the height of the habitat 2102. For instance, the height of the insert 2000 may be approximately 5 inches less than the height of the habitat 2102. In other cases, the height of the insert 2000 may be between approximately 3 inches and 7 inches less than the height of the habitat 2102. In one specific example, the height of the habitat may be 14 inches tall and the height of the insert 2000 may be 9 inches.

Figure 22:
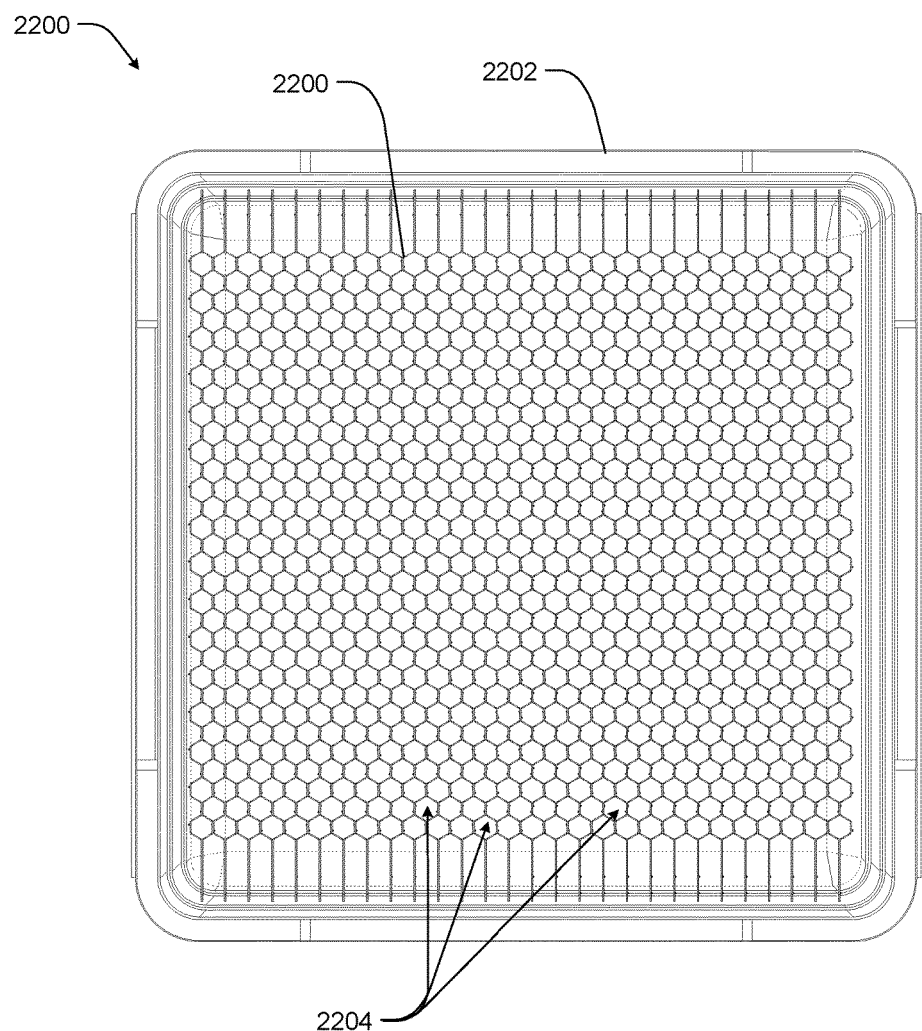
FIG. 22 illustrates an example overhead view of the insert of FIG. 20 within a habitat according to some implementations.

FIG. 22 illustrates an example overhead view of the insert 2000 of FIG. 20 within a habitat 2202 according to some implementations. In the illustrated example, the hexagonal openings, generally indicated by 2204, forming the hexagonal grid are visible. In the current example, the habitat 2202 and the insert 2000 are shown as an approximate equal in length and width. However, it should be understood that any length or width of habitat 2202 and insert 2000 may be selected. For instance, in one specific example, the habitat 2202 may be approximately three feet or 36 inches in width and length and the insert 2000 may be formed from vertical members having an approximant length of 872 mm or 34 inches. Thus, the insert 2000 may be configured to be 872 mm by 872 mm to fit within the three-foot habitat 2202.

Figure 23:
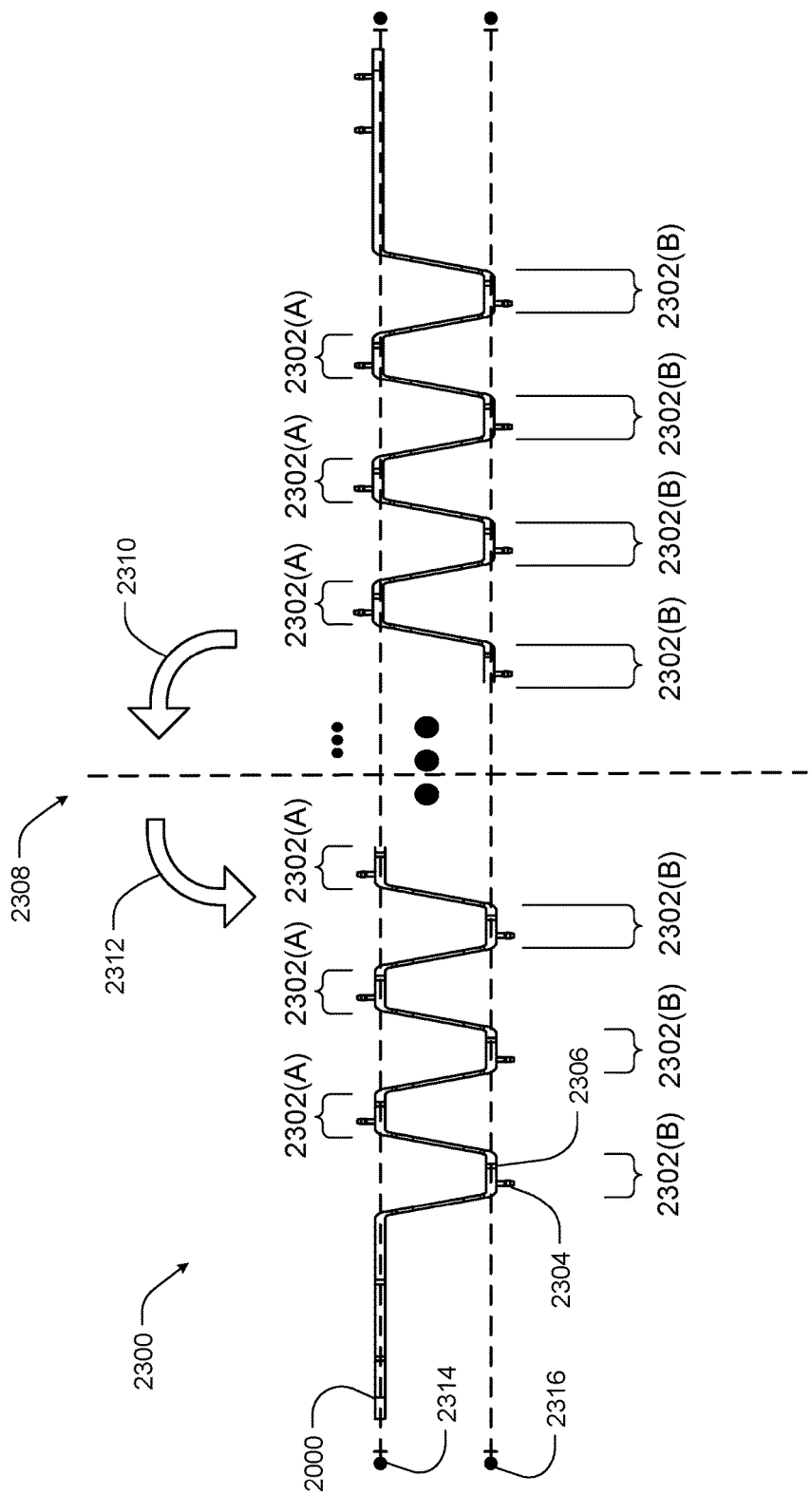
FIG. 23 illustrates an example overhead view of a vertical member of the insert of FIG. 20 according to some implementations.

In the current example, the hexagonal openings 2204 may be formed from six interior angles being approximately 120° and from members of approximal equal length. However, in other examples, the hexagonal openings 2204 may be formed from members having different lengths and, thus, different angles that total 720°. For instance, the interior angels may include two angles of 160° and four angles of 100°. FIG. 23 illustrates an example overhead view of a vertical member 2300 of the insert 2000 of FIG. 20 according to some implementations. In the illustrated example, the vertical member 2300 forms a plurality of half hexagon openings, generally indicated by 2302. The plurality of half hexagon openings 2302 include a plurality of top half hexagon openings 2302(A) and a plurality of bottom half hexagon openings 2302(B). Thus, when the vertical member 2300 is mated with a second vertical member (not shown) above the vertical member 2300, the plurality of bottom half hexagon openings 2302(B) form hexagons with respect to a plurality of top half hexagon openings of the second vertical member. Likewise, when the vertical member 2300 is mated with a third vertical member (not shown) below the vertical member 2300, the plurality of top half hexagon openings 2302(A) form hexagons with respect to a plurality of bottom half hexagon openings of the second vertical member.

Each of the plurality of half hexagon openings 2302 may also include male connector and a female connector, such as male connector 2304 and female connector 2306. Thus, when the second and/or third vertical members are mated with the vertical member 2300, the male connectors mate with corresponding female connectors on the second and/or third vertical members and the female connectors mate with corresponding male connectors on the second and/or third vertical members. For example, the male connector 2304 may mate with a female connector on the third vertical member and the female connector 2306 may mate with a male connector on the third vertical member to form the hexagonal grid.

In the current example, the male connector 2304 and the female connector 2306 are shown. However, it should be understood that the male and female connectors 2304 and 2306 may take various forms such as hook and loop connectors, snaps, pins, locking members, ties, among others. Additionally, it should be noted that in the current example, the male connectors are to the left of the female connectors for each of the plurality of top half hexagon openings 2302(A) and each of the plurality of bottom half hexagon openings 2302(B). In this example, the arrangement of male connectors to female connectors is appropriate as each vertical member, including member 2300, is approximately identical and configured to be rotated by 180° about the axis 2308 in the direction indicated by 2310 and 2312 to cause the male and female connectors on member 2300 and the second and/or third member to align correctly, as will be described in more detail with respect to FIG. 24 below.

For example, the vertical member 2300 may include a first plane 2314 configured to mate with the subsequent vertical member and a second plane 2316 configured to mate with the preceding vertical member. In the current example, the male and female connectors are all arranged in an identical fashion, however, in other examples, the male and female connectors on the first plane 2314 may differ from the arrangement of the male and female connectors on the second plane 2316.

Figure 24:
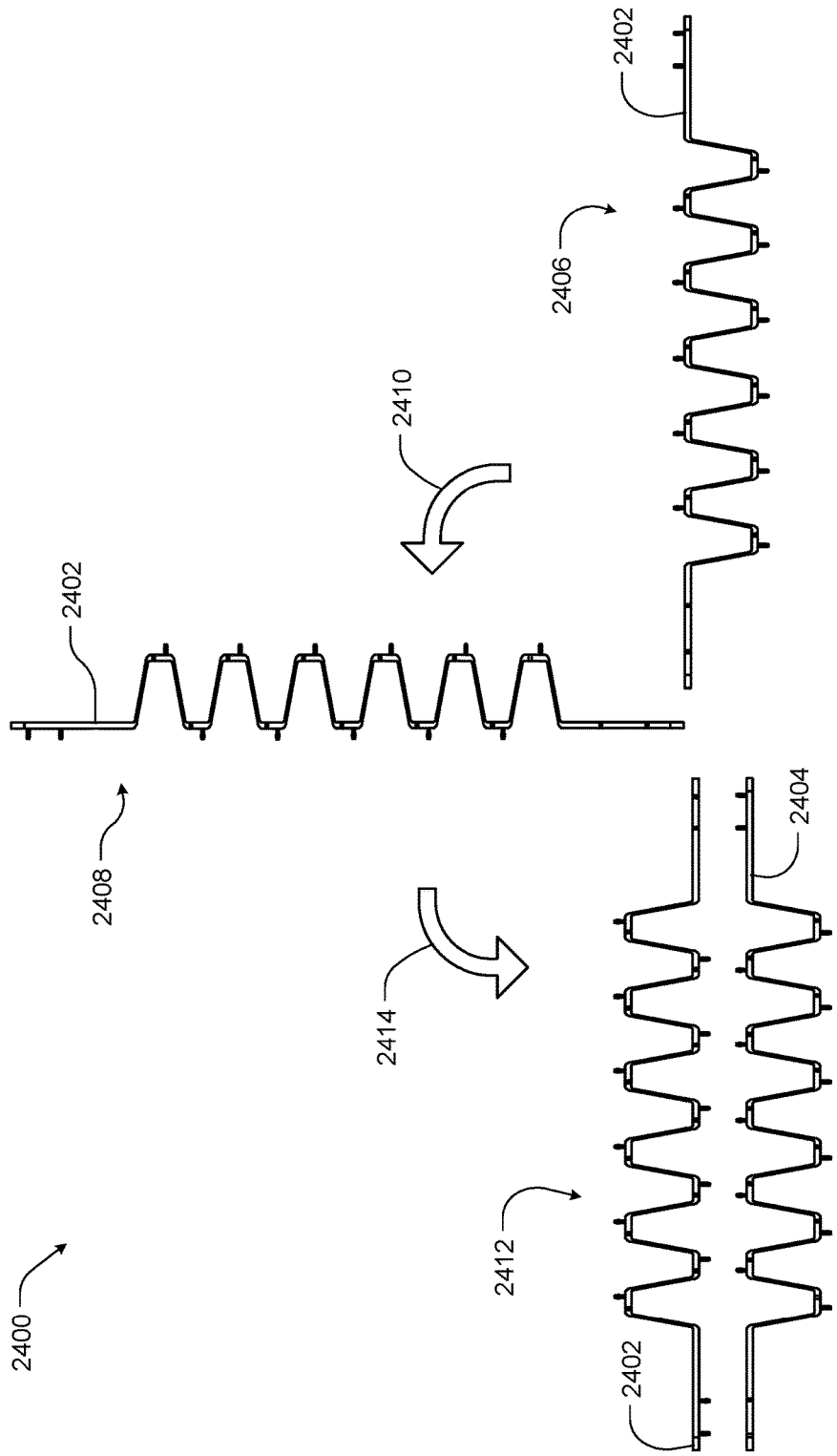
FIG. 24 illustrates an example overhead view of a first vertical member being alighted to connect with a second vertical member according to some implementations.

FIG. 24 illustrates an example overhead view 2400 of a first vertical member 2403 being aligned to connect with a second vertical member 2404 according to some implementations. For instance, in the current example, the first and second vertical members 2402 and 2404 are substantially identical to each other, such that each may be formed from a single mold or die. However, as illustrated, the first vertical member 2402 may first be rotated 90° from a first position 2406 to a second position 2408 along path 2410. The first vertical member 2402 may then be rotated an additional 90° (e.g., 180° total) to a third position 2312 along path 2414 to cause the male and female connectors of the first vertical member 2402 to align with the male and female connectors of the second vertical member 2404. Thus, as shown, an insert may be formed from substantially identical vertical members that may be machined, molded, cast, or otherwise formed via a single die, thereby reducing the overall costs associated with manufacturing the insert.

Figure 25:
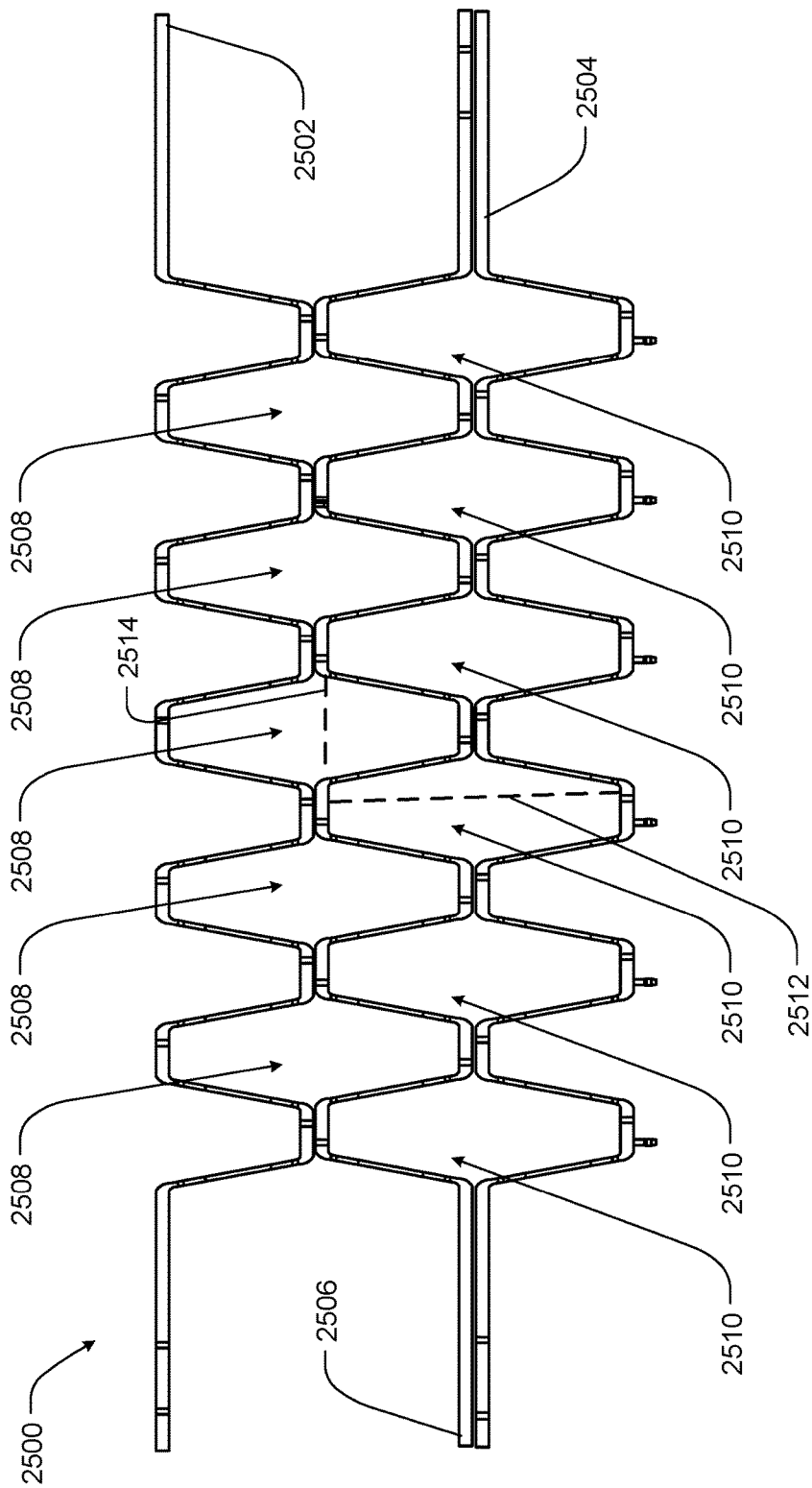
FIG. 25 illustrates a partial overhead view of an example insert having a first vertical member and a second vertical member coupled to a third vertical member according to some implementations.

FIG. 25 illustrates a partial overhead view of an example insert 2500 having a first vertical member 2502 and a second vertical member 2504 coupled to a third vertical member 2506 according to some implementations. In the current example, the wall of the first vertical member 2502 and the third vertical member 2506 form a first set of hexagonal regions 2508 and the second vertical member 2502 and the third vertical member 2506 form a second set of hexagonal regions 2510. Thus, it should be understood that each of the vertical members 2502-2506 from a first set of half hexagonal regions and a second set of half hexagonal regions.

The hexagonal regions 2508 and 2510 may be an open space that runs vertically through the insert 2500 to allow the insects vertical space in which to live. In general, the distance 1512 between the top of a hexagonal region and the bottom of a hexagonal region may vary from 10 mm to 40 mm measured for instance along the axis 2512. In one example, the distance 2512 may be 26.5 mm. Likewise the distance 2514 between the sides of the hexagonal regions may also vary from 10 mm to 40 mm.

Figure 26:
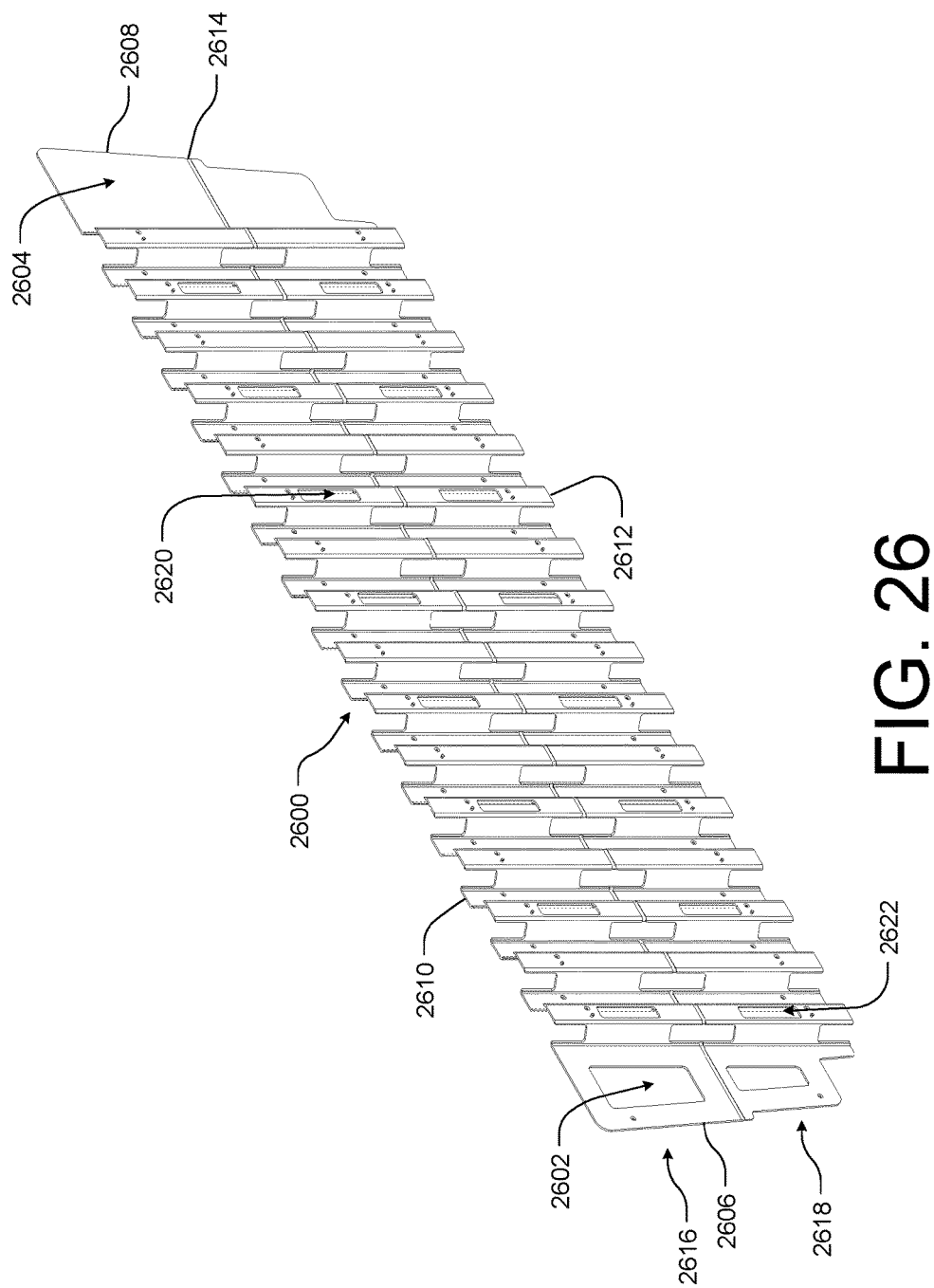
FIG. 26 illustrates an example side view of a vertical member according to some implementations.

FIG. 26 illustrates an example side view of a vertical member 2600 according to some implementations. In the current example, the vertical member 2600 includes openings, such as openings 2602 that are configured to align with solid portions, such as solid portion 2604 when the vertical member 2600 is connected or mated to a second vertical member to form an insert. Thus, as configured when the member 2600 is rotated to align with a second vertical member as discussed above with respect to FIGS. 23 and 24, the opening 2602 of the vertical member 2600 align with the solid portion 2504 of the second member, thereby closing off the opening 2602 and preventing an insect from moving through the opening 2604. Thus, in this example, the amount of material used to create or generate each individual vertical member may be reduced by removing some material at locations where the openings will coincide with solid portions of another vertical member when fully assembled.

The exterior or side walls 2606 and 2608 of the vertical member 2600 may also be formed with a sloping shape. For instance, the habitats configured to receive the inserts formed with the vertical members, such as vertical member 2600, may be slopped or tapered to increase the overall difficult associated with an insect escaping or exciting the habitat. Thus, in some examples, each of the vertical members 2600 may be configured to also tapper or slope. In the current example, the vertical member 2600 may be 36 inches in length along a top surface 2610 and 33 inches in length along a bottom surface 2612.

In some specific examples, the insert 2600 may also include a snap line 2614. The snap line 2614 may be positioned approximately half way between a top surface and a bottom surface of the vertical member 2600. The snap line 2614 may be used to break or divide the vertical member 2600 into two individual vertical members, generally indicated by top member 2616 and bottom member 2618. In some case, the top member 2616 may include at least one perforation, such as perforation 2620, and the bottom member 2618 may include at least one perforation, such as perforation 2622. In some examples, the height of the top member 2616 and the height of the bottom member 2618 may be greater than or equal to 3 inches.

Figure 27:
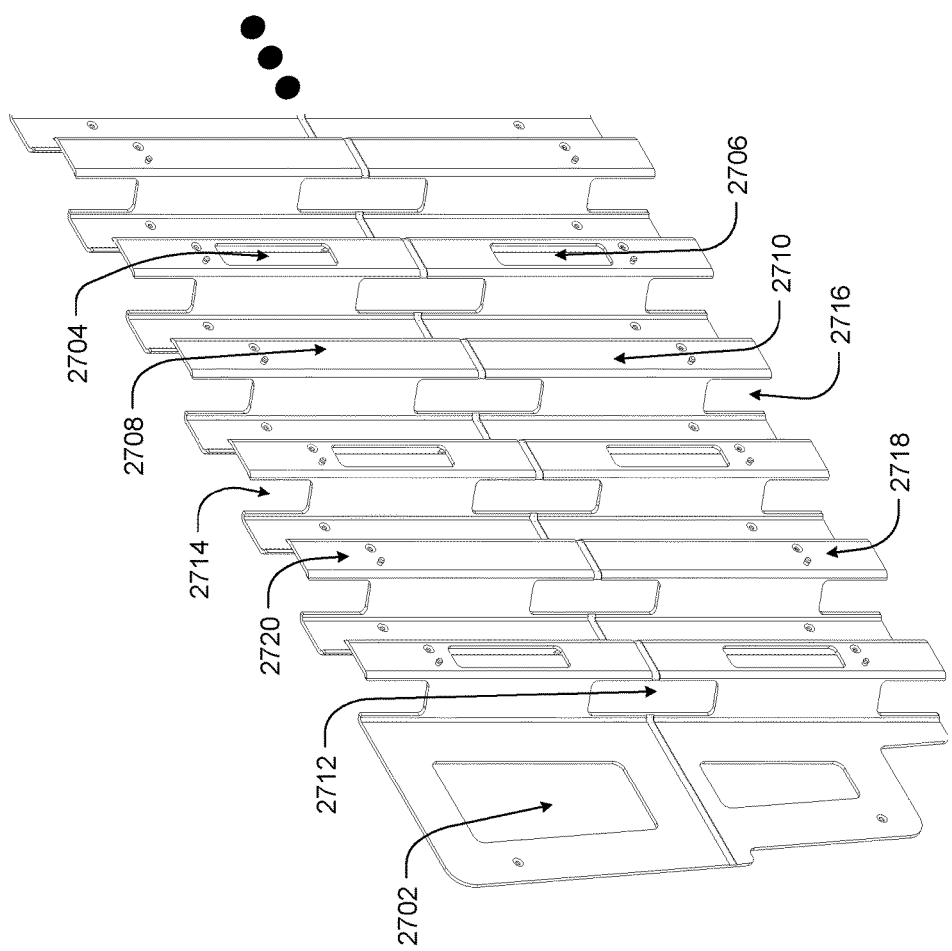
FIG. 27 illustrates an example partial side view of a vertical member according to some implementations.

FIG. 27 illustrates an example partial side view of a vertical member 2700 according to some implementations. As discussed above with respect to FIG. 26, the vertical member 2700 may include openings, such as opening 2702, 2704, or 2706 that are configured to align with solid portions, such as solid portions 2708 or 2710 when the vertical member 2700 is assembled into an insert. However, the vertical member 2700 may also include openings, such as openings 2712, 2714, and 2716 that are configured to remain open when the vertical member 2700 is assembled into an insert. The openings 2712, 2714, and 2716 may be used by the insects cultivated within a habitat to move through the habitat and reach destinations such as feed or water trays or stations. A the same time, by limiting the size of the openings 2712, 2714, and 2716 the insects ability to traverse the habitat may be partially limited, thereby reducing the risk of spreading diseases or other pathogens through the entire population.

In some cases, the openings 2712, 2714, and 2716 may be 45 mm tall and 10 mm wide. In other cases, the openings 2712, 2714, and 2716 may be as small as 10 mm by 10 mm or as large as 60 mm by 60 mm. In some implementations, the openings 2712, 2714, and 2716 may be nonuniform in size to further control the insects movements through the habitat.

The vertical member 2700 also includes connectors, generally indicate by 2718 and 2720, positioned at both the top and bottom of the vertical member 2700. For instance, positioning connectors at the top and bottom of the vertical member 2700 may prevent the vertical members 2700 of the insert from separating or otherwise disconnecting during use.

Figure 28:
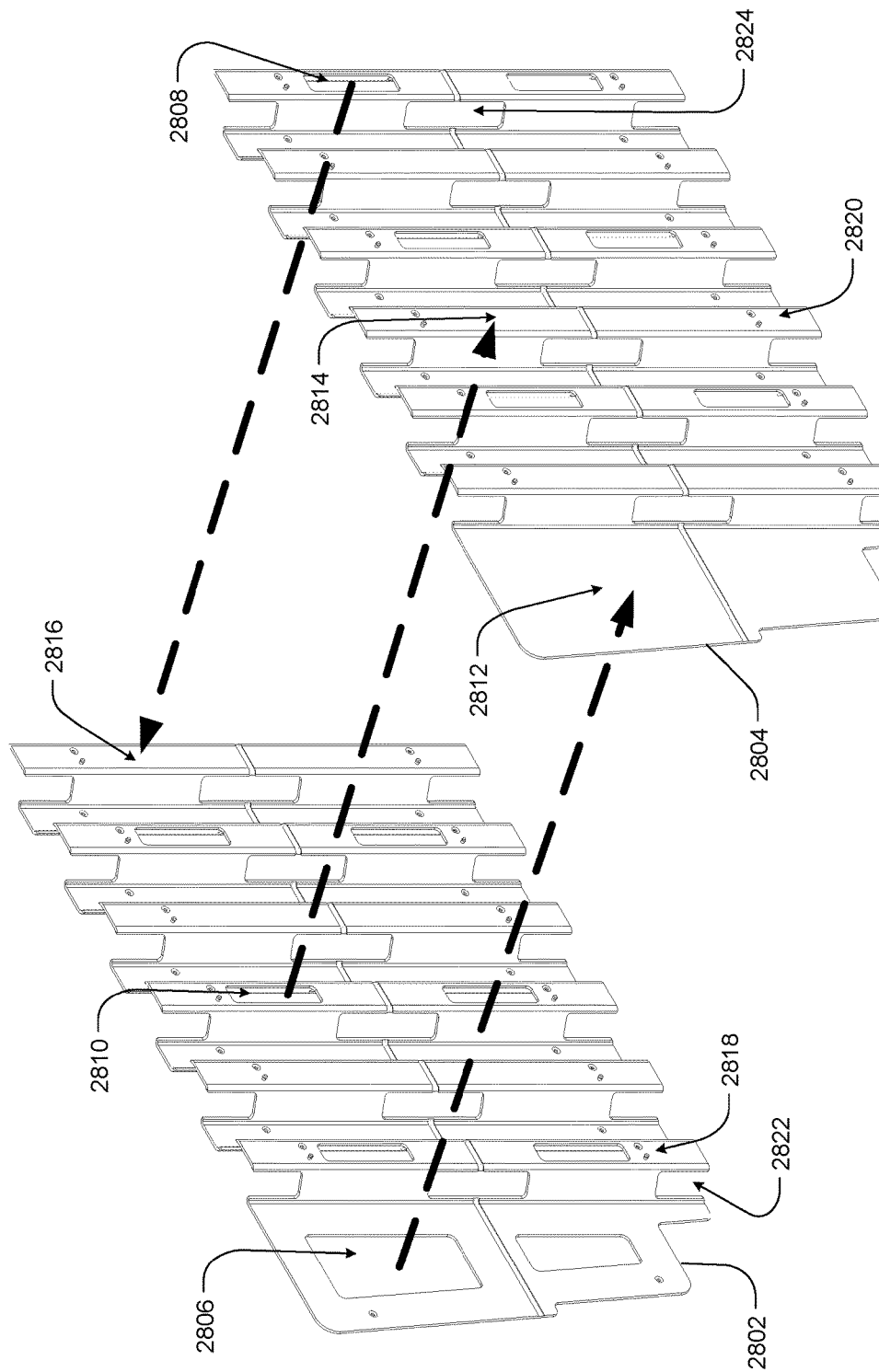
FIG. 28 illustrates an example partial side view of a first vertical member and a second vertical member according to some implementations.

FIG. 28 illustrates an example partial side view of a first vertical member 2802 and a second vertical member 2804 according to some implementations. As discussed above, each of the members of an insert, such as members 2802 and 2804, may include openings or gaps, generally indicated by 2806, 2808, and 2810, that are configured to mate with closed or filled portions, generally indicated by 2812, 2814, and 2816, of the opposing, subsequent, or mating member. Thus, when the members 2802 and 2804 are mated or connected via pins, generally indicated by 2818 and 2820, the openings 2804, 2806, and 2808 are closed and thereby prevent improving structural support and preventing insect migration through the openings 2804, 2806, and 2808.

Further, it should be understood, that while openings 2804, 2806, and 2808 or the openings along mating walls of the members 2802 and 2804 may be closed or sealed when the insert is fully assembled, other openings, such as openings 2722 and 2824 may remain open when the insert is fully assembled. Thus, the opening, such as openings 2822 and 2824, may be configured to allow the insects to move through or otherwise traverse an insert. Alternatively, the openings 2804, 2806, and 2808 allow for a reduction in manufacturing costs while maintaining structural stability when the insert is fully assembled.

FIG. 29 illustrates an example of an insert 2902 removed from a habitat 2904 according to some implementations. The insert 2902 may be included in the habitat 2904 to increase the overall total surface area within the same volume previously contained within the habitat 2904, as the increase in surface area results in a corresponding increase in the insects that may be cultivated within the same volume of space. In the illustrated example, the insert 2902 may generally form a grid, helix or cross-section within the interior space of the habitat 2904.

As shown in the illustrated example, the insert 2902 may be removable from the habitat 2904 and include vertical walls or members that allow the insert 2902 to be shaken to be dislodged or removed from the habitat 2904 during harvesting in a more efficient manner. For example, the insert 2902 may be moved over a collection bin and vibrated to cause the insects to fall off of or detach from the surfaces of the insert 2902.

In the current example, the insert 2902 and the habitat 2904 each have slopping exterior or side walls, generally indicated by 2906, 2908, 2910, and 2912. In general, the slopping of the side walls 2910 and 2912 are included to prevent the insects within the habitat 2904 from climbing or otherwise escaping. In some cases, the side walls 2910 and 2912 may also be coated or formed from a material having a low coefficient of friction to further prevent the insects from escaping the habitat 2904.

In some examples, described herein, a rack system for holding habitats for cultivating insects may be configured to include a first level having a track for allowing a first set of habitat to move to individual locations associated with a first set of habitat stations. The rack system may also include a second level positioned over the first level and also having a track for allowing a second set of habitats to move to individual locations associated with a second set of habitat stations. In some cases, each of the habitat stations are associated with a feeding dispenser, a water dispenser, and a lighting device. The rack system may also include a loading zone and an unloading zone for each level. In one implementation, the rack system include a latching device adjacent to each of the unloading zones to prevent the habitats from being unintendedly unloaded from the rack.

In one example, a habitat for housing insects may include at least one side wall having an interior surface with a coefficient of friction less than 0.5 and a bottom portion coupled to the at least one side wall to defining an interior area for containing insects. In some cases, the habitat may include a cantilevered lip extending outward from a top portion of the at least one side wall to engage with a rack system, as discussed above. In some cases, the side wall(s) may be formed from a non-porous material and, in some instance, the side wall may be inclined inwardly starting from the cantilevered lip to the bottom portion by less than or equal to 10 degrees.

In some cases, the habitats may have an opening at the top to expose the habitat to the surrounding environment. In this example, the habitat may be configured to receive a habitat insert as discussed above to increase the overall volume for cultivating the insects within the habitat. In some cases, the insect habitat insert may be formed from a plurality of vertical components or members, the vertical members may be interlocking or mating to form a grid within the habitat.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A insect habitat insert comprising:
a first plurality of vertical components, the first plurality of vertical components including locking slits along a bottom of each of the first plurality of vertical components; and
a second plurality of vertical components, the second plurality of vertical components including locking slits along a top of each of the second plurality of vertical components, wherein the locking slits along the top of each of the second plurality of vertical components mate with the locking slits along the bottom of each of the first plurality of vertical components to form a grid.

2. The insect habitat insert as recited in claim 1, wherein the insect habitat insert is configured to fit within an habitat for cultivating insects.

3. The insect habitat insert as recited in claim 1, wherein the first plurality of vertical components are perforated.

4. The insect habitat insert as recited in claim 1, wherein the second plurality of vertical components are perforated.

5. The method as recited in claim 1, wherein a coefficient of friction associated with the first plurality of vertical components and the second plurality of vertical components is greater than 0.5.

6. A insect habitat insert comprising:
a plurality of vertical members for the cultivating of insects, each of the vertical members defining a first half set of hexagonal regions and a second half set of hexagonal regions, such that when the plurality of vertical members are arranged in parallel, the plurality of vertical members from a hexagonal grid, the hexagonal grid including a plurality of hexagonal regions.

7. The insect habitat insert as recited in claim 6, wherein each of the vertical members are substantially identical.

8. The insect habitat insert as recited in claim 7, wherein the vertical members includes a first vertical member and a second vertical member, the first vertical member including a first a plurality of male connectors arranged to the right of a first plurality of female connects and the second vertical member including a second a plurality of male connectors arranged to the right of a second plurality of female connects, such that the first vertical member mates with the second vertical member when the first vertical member is rotated by 180° around a center vertical axis with respect to the second vertical member.

9. The insect habitat insert as recited in claim 7, wherein the plurality of vertical members includes a first vertical member and a second vertical member, the first vertical member including a first a plurality of male connectors arranged to the left of a first plurality of female connects and the second vertical member including a second a plurality of male connectors arranged to the left of a second plurality of female connects, such that the first vertical member mates with the second vertical member when the first vertical member is rotated by 180° around a center vertical axis with respect to the second vertical member.

10. The insect habitat insert as recited in claim 6, wherein the insect habitat insert is configured to fit within a habitat for cultivating insects.

11. The insect habitat insert as recited in claim 6, wherein individual ones of the vertical members include perforations for allowing the insects to traverse the hexagonal grid.

12. The insect habitat insert as recited in claim 6, wherein the plurality of vertical members includes a first vertical member and a second vertical member, the first vertical member including a first plurality of open portions and a first plurality of solid portions and the second vertical member including a second plurality of open portions and a second plurality of solid portions, the first plurality of open portions configured to align with the second plurality of solid portions and the second plurality of open portions configured to align with the first plurality of solid portions when the first vertical member mates with the second vertical member.

13. The method as recited in claim 12, wherein first vertical member is rotated by 180° around a center vertical axis with respect to the second vertical member prior to mating the first vertical member with the second vertical member.

14. The method as recited in claim 6, wherein each of the hexagonal regions is less than or equal to 40 mm across.

15. A vertical member of an insect habitat insert comprising:
a first set of mating portions along a first plane;
a second set of mating portions along a second plane, the first set of mating portions to be arranged adjacent to a preceding vertical member and the second set of mating portions to be arranged adjacent to a subsequent vertical member when the insect habitat insert is fully assembled;

a plurality of interior portions connecting the first set of mating portion to the second set of mating portions; and wherein the plurality of interior portions, the first set of mating portions, and the second set of mating portions form a continuous wall, the continuous wall defining a first set of open regions and a second set of open regions when the insect habitat insert is fully assembled, the first set of open regions located on an opposite side of the continuous wall as the second set of open regions.

16. The insect habitat insert as recited in claim 15, wherein at least one of the interior portions include an opening to allow an insect to traverse from an open region of the first set of open regions to an open region of the second set of open regions.

17. The insect habitat insert as recited in claim 15, wherein the continuous wall is equal to or less than 1.2 millimeters thick.

18. The insect habitat insert as recited in claim 15, wherein the vertical member is greater than or equal to 2 inches and less than or equal to 32 inches tall.

19. The insect habitat insert as recited in claim 15, wherein at least one of the open regions of the first set of open regions or the second set of open regions is hexagonal in shape.

20. The insect habitat insert as recited in claim 15, wherein the vertical member has a coefficient of friction greater than or equal to 0.5.

\* \* \* \* \*